United States Patent
Von Drasek et al.

(10) Patent No.: US 10,604,896 B2
(45) Date of Patent: *Mar. 31, 2020

(54) METHOD FOR EARLY WARNING CHATTER DETECTION AND ASSET PROTECTION MANAGEMENT

(71) Applicant: Ecolab USA Inc., Saint Paul, MN (US)

(72) Inventors: William A. Von Drasek, Oak Forest, IL (US); Gary S. Furman, Jr., St. Charles, IL (US); Sammy L. Archer, Naperville, IL (US)

(73) Assignee: Ecolab USA Inc., Saint Paul, MN (US)

( * ) Notice: Subject to any disclaimer, the term of this patent is extended or adjusted under 35 U.S.C. 154(b) by 213 days.

This patent is subject to a terminal disclaimer.

(21) Appl. No.: 15/225,199

(22) Filed: Aug. 1, 2016

(65) Prior Publication Data

US 2016/0340830 A1 Nov. 24, 2016

Related U.S. Application Data

(63) Continuation of application No. 13/277,545, filed on Oct. 20, 2011, now Pat. No. 9,404,895.

(51) Int. Cl.
*D21G 9/00* (2006.01)
*D21G 3/00* (2006.01)
(Continued)

(52) U.S. Cl.
CPC .............. *D21G 9/0036* (2013.01); *D21G 3/00* (2013.01); *D21G 3/04* (2013.01); *D21G 9/0045* (2013.01);
(Continued)

(58) Field of Classification Search
CPC ...... D21G 9/0036; D21G 9/0045; D21G 3/04; D21G 3/00; G06N 7/08; G06N 3/02;
(Continued)

(56) References Cited

U.S. PATENT DOCUMENTS 3,061,944 A 11/1962 Kraus et al.
4,320,582 A 3/1982 Klippstein et al.
(Continued)

FOREIGN PATENT DOCUMENTS

CN 202401341 U 8/2012
CN 103194927 B 5/2015
(Continued)

OTHER PUBLICATIONS

Claveau et al, Mechanical Vibration Analysis Using an Optical Sensor, 'National Optics Institute', IEEE,CCECE'96 0-7803-31431-5, pp. 876-879 (Year: 1996).*
(Continued)

*Primary Examiner* — Lisa E Peters
(74) *Attorney, Agent, or Firm* — Fredrikson & Byron, P.A.

(57) ABSTRACT

The invention embodies the application of different combinations of the monitoring and data processing aspects as a means to develop an early warning chatter alarming system. Configuring an early warning chatter alarming system can be as simple as using no alarm settings to develop an alarming strategy from different trend conditions such as overall RMS, selected vibration frequencies, slope analysis, and wavelet analysis. A higher level of alarming is provided by using a time integrated approach to account for both intensity of the alarm variable and duration. Combining these different aspects with a predictive model incorporates process-operating conditions to enhance the alarming sensitivity for earlier detection and reduce false positives. Finally, combining the different alarming aspects with a rule-based decision making approach such as fuzzy logic allows alarming based on qualitative analysis of different data streams.

20 Claims, 18 Drawing Sheets

(51) Int. Cl.
| | | |
|---|---|---|
| G01N 29/44 | (2006.01) | |
| G01N 29/46 | (2006.01) | |
| G01N 29/14 | (2006.01) | |
| D21G 3/04 | (2006.01) | |
| G06N 3/02 | (2006.01) | |
| G06N 7/08 | (2006.01) | |

(52) U.S. Cl.
CPC .......... *G01N 29/14* (2013.01); *G01N 29/4418* (2013.01); *G01N 29/4481* (2013.01); *G01N 29/46* (2013.01); *G06N 3/02* (2013.01); *G06N 7/08* (2013.01)

(58) Field of Classification Search
CPC .............. G01N 29/14; G01N 29/4418; G01N 29/4481; G01N 29/46
See application file for complete search history.

(56) References Cited

U.S. PATENT DOCUMENTS

| | | | | |
|---|---|---|---|---|
| 4,924,420 | A | * | 5/1990 | Hadley ............... G06F 7/68 324/160 |
| 5,123,152 | A | | 6/1992 | Tenkula et al. |
| 5,179,150 | A | | 1/1993 | Furman et al. |
| 5,187,219 | A | | 2/1993 | Furman et al. |
| 5,278,620 | A | | 1/1994 | Godlove |
| 5,571,382 | A | | 11/1996 | Berglund et al. |
| 5,879,279 | A | * | 3/1999 | Berger ............... B04B 9/146 494/11 |
| 6,139,686 | A | * | 10/2000 | Trokhan ............. D21F 5/004 162/109 |
| 6,203,962 | B1 | | 3/2001 | Itami et al. |
| 6,260,004 | B1 | * | 7/2001 | Hays ............... G05B 23/0235 702/130 |
| 6,275,781 | B1 | * | 8/2001 | Maness ............... G01M 13/045 702/182 |
| 6,463,775 | B1 | | 10/2002 | Kodama et al. |
| 6,615,709 | B1 | | 9/2003 | Suomi et al. |
| 6,928,370 | B2 | | 8/2005 | Anuzis et al. |
| 7,027,953 | B2 | * | 4/2006 | Klein ............... G01H 1/006 702/182 |
| 7,286,964 | B2 | | 10/2007 | Kim |
| 7,691,236 | B2 | | 4/2010 | Conn et al. |
| 7,850,823 | B2 | | 12/2010 | Chou et al. |
| 7,962,086 | B2 | | 6/2011 | Kato |
| 8,160,467 | B2 | | 4/2012 | Zona et al. |
| 9,194,083 | B2 | | 11/2015 | Echeverria et al. |
| 9,239,549 | B1 | | 1/2016 | Ishii |
| 9,506,192 | B2 | | 11/2016 | Johnson et al. |
| 9,518,359 | B2 | | 12/2016 | Brauns et al. |
| 9,534,970 | B1 | | 1/2017 | Figiel |
| 9,562,861 | B2 | | 2/2017 | Von Drasek et al. |
| 2004/0035540 | A1 | | 2/2004 | Maeenpaeae et al. |
| 2005/0034831 | A1 | | 2/2005 | Beuther et al. |
| 2005/0157327 | A1 | | 7/2005 | Shoji et al. |
| 2006/0090574 | A1 | | 5/2006 | Moore et al. |
| 2006/0182451 | A1 | | 8/2006 | Shoji et al. |
| 2006/0281191 | A1 | | 12/2006 | Duggirala et al. |
| 2007/0125891 | A1 | | 6/2007 | Crossley et al. |
| 2007/0127934 | A1 | | 6/2007 | Shoji et al. |
| 2007/0137820 | A1 | | 6/2007 | Yasugahira et al. |
| 2008/0013818 | A1 | | 1/2008 | Shakespeare |
| 2008/0023168 | A1 | | 1/2008 | Conn et al. |
| 2008/0033695 | A1 | * | 2/2008 | Sahara ............... G01H 1/003 702/185 |
| 2009/0190939 | A1 | * | 7/2009 | Satoh ............... G03G 21/0011 399/34 |
| 2010/0086672 | A1 | * | 4/2010 | Von Drasek ....... B31F 1/14 427/9 |
| 2010/0299119 | A1 | * | 11/2010 | Erikson ............... E21B 43/01 703/6 |
| 2012/0073775 | A1 | | 3/2012 | Duggirala et al. |
| 2015/0075928 | A1 | | 3/2015 | Johnson et al. |
| 2019/0120811 | A1 | | 4/2019 | Luneau et al. |

FOREIGN PATENT DOCUMENTS

| | | |
|---|---|---|
| DE | 102005052858 A1 | 5/2007 |
| DE | 202009008818 U1 | 11/2009 |
| DE | 102011085220 A1 | 5/2012 |
| FI | 115145 B | 3/2005 |
| GB | 1577664 A | 10/1980 |
| JP | S5609493 A | 1/1981 |
| JP | 11012977 A | 1/1999 |
| JP | 201112977 | 1/1999 |
| JP | 3117936 B2 | 12/2000 |
| JP | 2001523774 A | 11/2001 |
| JP | 2010217512 A | 9/2010 |
| WO | 2004005615 A1 | 1/2004 |
| WO | 2004040983 A1 | 5/2004 |
| WO | 2011002377 A1 | 1/2011 |
| WO | 2012055897 A1 | 5/2012 |
| WO | 2013156147 A1 | 10/2013 |

OTHER PUBLICATIONS

English Machine Translation of Japanese Application No. 2010217512, published Sep. 30, 2010, 20 pages.

Japanese Application No. 2001523774, published as WO99-25921, published May 27, 1999, 23 pages.

English Machine Translation of Japanese Application No. 201112977, published Jan. 19, 1999, 14 pages.

Agarwal, Asynchronous Analog to Digital Converters: Architectures and Circuits, Aug. 2010, pp. 1-112.

Alessandrini, A. 7 Pagani, P., "Chatter Marks: Origin, Evolution and Influence of the Creping Doctors," Ind. Carta, vol. 41, No. 4, Jun. 2003, pp. 120-129.

Arato, Jr., A., Lobato de Almeida, F.C., "Automatic faults diagnosis by application of neural network system and condition-based monitoring using vibration signals," Proceedings of the 2008 IAJC-IJME International Conference, ISBM 978-1-60643-379-9.

Archer, S., Grigoriev, V. Furman, G., Bonday, L. and Su, W. "Chatter and Soft tissue Production: Process Driven Mechanisms," Tissue World Americas, Feb.-Mar. 2009, pp. 33-35.

Fugate, M., Sohn, H., & Farrar, C., "Vibration-ased damage detection using statistical process control," Mechanical Systems and Signal Processing, vol. 15, Issue 4, Jul. 2001, pp. 707-721.

Heng, A., Zhang, S., Tan, A., and Mathew, J., "Rotating machinery prognostics: State of the art, challenges and opportunities," Mechanical Systems and Signal Processing, vol. 23, 2009, pp. 724-739.

Jeong et al., A Fault Diagnosis on Rotating Machinery Using the Mahalanobis Taguchi System, Mechanical Engineering Department, Hanyang University, Korea, Jul. 2009, 7 pages.

Koichi Akazawa et al., Study on Regenerative Chatter Vibration in Ball End Milling of Flexible Workpieces, 2008, 6 pages.

Messaoud, A.,Weihs, C., and Hering, F., "Detection of chatter vibration in a drilling process using multivariate control charts," Computational Statistics & Data Analysis, vol. 52, 2008, pp. 3208-3219.

Rehorn, A.G., Jiang, J., Orban, P., "State-of-the-art methods and results in tool doncition monitoring: review," International Jouranl of Advanced Manufacturing Technologies, vol. 26, 2005, pp. 693-710.

Shankar Jagannathan, Ph.D., Test and theory for robust active vibration control of rotor-bearing systems utilizing piezoelectric actuators, 1993, 213 pages.

Sohn, H., Farrar, C., "Damage diagnosis using time series analysis of vibration signals," Smart Materials and Structures, vol. 10, 2001, pp. 446-451.

Wichklin, What is Mahalanobis Distance, SAS Institute Inc., Feb. 15, 2012, 12 pages.

Zhang, S., Mathew, J., Ma, L., Sun, Y. and Mathew, A., "Statistical condition monitoring based on vibration signals," Proceedings VETOMAC-E & ACISM-2004, pp. 1238-1243, New Delhi, India.

ANON, (62nd) Pulp and Paper Research Conference, Tokyo, Japan, Jun. 1-2, 1995, Japan TAPPI, 1995, 156 pages, Abstract Only.

(56) References Cited

OTHER PUBLICATIONS

Beck, "Stickies in recycle pulp for use in fine paper—the search for a precise method," TAPPI Press, Recycling Symposium, New Orleans, Mar. 3-6, 1996, pp. 271-277, Abstract Only.
Bomela et al., "Effect of stator chording and rotor skewing on performance of reluctance synchronous machine," IEEE Transactions on Industry Applications (Jan. 2002), vol. 38, No. 1, pp. 91-100, Abstract Only.
Bomela et al., "Effect of machine design on performance of reluctance synchronous machine," Conference Record of the 2000 IEEE Industry Applications Conference. Thirty-Fifth IAS Annual Meeting and World Conference on Industrial Applications of Electrical Energy, Rome, Italy, 2000, vol. 1, pp. 515-522, Abstract Only.
Bomela et al., "Effect of stator chording and rotor skewing on average torque and torque ripple of reluctance synchronous machine," 1999 IEEE Africon. 5th Africon Conference in Africa, Cape Town, South Africa, 1999, vol. 2, pp. 687-690, Abstract Only.
Douek et al., "Some aspects of pitch control with talc in unbleached kraft pulps," Journal of Pulp and Paper Science, vol. 17, No. 5, 1991, pp. 171-177, Abstract Only.
EP Pat. App. No. 12841129.5, Extended European Search Report dated May 7, 2015, 5 pages.
Goryacheva et al., "Mechanical-chemical methods for the deresinification of pulp," Bumazhnaya Promyshlennost (1976), (3), 11, Abstract Only.
Herbst, "Construction of paper: to survive processing," PTS Symposium 2008: paper and imaging, Munich, Germany, Oct. 15-16, 2008, 22 pages, Abstract Only.
Holopainen et al., "Online machinery condition monitoring avoids unexpected failures and improves operator safety," Appita Journal, vol. 58, No. 1, Jan. 2005, pp. 18-21, Abstract Only.
Holopainen et al., "Online machinery condition monitoring avoids unexpected failures and improves operator safety," Appita Journal, vol. 58, No. 1, Jan. 2005, pp. 18-21, Abstract Only, (PIRA).
Hyvarinen et al., "Infrared analyzers for process measurements," Proceedings of SPIE—The International Society for Optical Engineering, vol. 1762, 1992, pp. 187-192, Abstract Only.
International Patent Application No. PCT/US2012/059631, International Search Report and Written Opinion dated Mar. 29, 2013, 6 pages.
International Patent Application No. PCT/US2012/059451, International Search Report and Written Opinion dated Mar. 29, 2013, 7 pages.
Kerman, "Fixative selection and runnability optimization in different paper grades using the Ciba Contaminant Analyzer (CCA)," Progress 08. 16th International papermaking conference. Efficiency in papermaking and converting Processes, Krakow, Poland, Sep. 23-26, 2008, 16 pages, Abstract Only.
Kermann et al., "Novel approach for the selection and optimisation of fixatives for pitch and sticky control in various fibre systems," 17th PTS CHT symposium: chemical technology of papermaking, Munich, Germany, Sep. 12-15, 2006, Paper 34, 21 pages, Abstract Only.
Kosuga et al., "Reduction of Pitch Deposit Troubles by Coagulant Derived from Waste Corrugated Board," Japan Tappi Journal, vol. 58, No. 4, 2004, pp. 468-477, Abstract Only.
Kuny, "New sensors for online property measurements," Wochenbl. Papierfabr., vol. 134, No. 23-24, Dec. 2006, pp. 1415-1418.
Murcia, "Combining stickies monitoring and control in tissue manufacturing from recycled fiber," Tissue World Americas 2010—5th International Conference and Exhibition for the North and South American Tissue Business (2010), 9 page, Abstract Only.
Padley, "Maximising performance through state-of-the-art chemistry solutions," Int. Papwirtsch., No. 4, 2009, pp. 19-22, Abstract Only.
Shevchenko et al., "Combining stickies monitoring and control in recycling," TAPPI Press, 2010 TAPPI PEERS Conference and 9th Research Forum on Recycling (2010), vol. 1, pp. 809-854, Abstract Only.
Sithole et al., "A laboratory test to predict deposition in recycled paper making," TAPPI Press, Recycling Symposium, Chicago, Apr. 14-16, 1997, pp. 367-371, Abstract Only, (HCAPLUS).
Sithole et al., "A laboratory test to predict deposition in recycled paper making," TAPPI Press, Recycling Symposium, Chicago, Apr. 14-16, 1997, pp. 367-371, Abstract Only, (PIRA).
Vahasalo et al., "White Pitch Deposition and Styrene-butadiene-rubber Binder Content in Paper Mill Process Waters," Appita Journal, vol. 59, No. 4, Jul. 2006, pp. 280-284.
Voltaire et al. "Acoustic emission and tack of heat-set inks during selling on MWCpapers and fountain solution emulsification," Nordic Pulp & Paper Research Journal, vol. 22, No. 4, 2007, pp. 432-440, Abstract Only.
Voltaire et al., "Acoustic characterisation of film splitting in a HSWO printing nip," Nordic Pulp & Paper Research Journal, vol. 22, No. 4, 2007, pp. 424-431, Abstract Only.
Voltaire et al., "Use of an on-press acoustic sensor to monitor coldset offset printing of newspaper," Nordic Pulp & Paper Research Journal, vol. 21, No. 3, 2006, pp. 323-327, Abstract Only.
Voltaire et al., "Acoustic investigation of cavitation noise from offset ink film splitting," Nordic Pulp & Paper Research Journal, vol. 21, No. 3, 2006, pp. 314-322, Abstract Only.
Welkener et al., "The effect of furnish components on depositability of pitch and stickies," Nordic Pulp & Paper Research Journal, vol. 8, No. 1, 1993, pp. 223-225, Abstract Only.
Zwart et al., "The struggle for paper uniformity," TAPPI Press, International Engineering Conference, Miami, Sep. 13-17, 1998, vol. 1, pp. 243-251, Abstract Only.

\* cited by examiner

METHOD FOR EARLY WARNING CHATTER DETECTION AND ASSET PROTECTION MANAGEMENT

CROSS-REFERENCES

This application is a continuation of U.S. application Ser. No. 13/277,545, filed Oct. 20, 2011, the contents of which are hereby incorporated by reference in its entirety.

BACKGROUND OF THE INVENTION

The present invention relates to methods, compositions, and apparatuses for the detection and prevention of chatter in doctor blades on a Yankee dryer. As described at least in U.S. Pat. Nos. 7,691,236, 7,850,823, 5,571,382, 5,187,219, 5,179,150, 5,123,152, 4,320,582, and 3,061,944, in the tissue manufacturing process, a paper sheet is dried on a heated drying cylinder, termed a Yankee or Yankee dryer. Often adhesive materials are used to coat the Yankee surface in order to help the wet sheet adhere to the dryer. This improves heat transfer, allowing more efficient drying of the sheet. Most importantly, these adhesives provide the required adhesion to give good creping of the dry sheet. Creping is the process of impacting the sheet into a hard blade (called a doctor blade), thus compressing the sheet in the machine direction, creating a folded sheet structure. Creping breaks a large number of fiber-to-fiber bonds in the sheet, imparting the qualities of bulk, stretch, absorbency, and softness which are characteristic of tissue. The amount of adhesion provided by the coating adhesive plays a significant role in the development of these tissue properties.

In addition, the present invention covers detection and prevention of chatter in doctor blades used for cleaning residual coating from the Yankee surface as well as the cut-off doctor blade used during maintenance operations on the creping doctor blade. The present invention focuses on the creping operation, but extension of methodology to the cleaning and cut-off blade apply equally as well.

The Yankee coating also serves the purpose of protecting the Yankee and creping blade surfaces from excessive wear. In this role, the coating agents provide improved runabity of the tissue machine. As creping doctor blades wear, they must be replaced with new ones. The process of changing blades represents a significant source of tissue machine downtime, or lost production, as creped product cannot be produced when the blade is being changed. Release agents, typically hydrocarbon oils, are used in association with the coating polymers. These agents aid in the uniform release of the tissue web at the creping blades, and also lubricate and protect the blade from excessive wear.

Proper and sustained interaction between the Yankee coating and the creping doctor blade is critical for both sheet property development and machine runnability. In normal operations, the creping doctor blade tip rides in the coating on the dryer surface and experiences minimal out of plane movement. However, if the amplitude of the out of plane movement becomes high enough the creping doctor blade wilt oscillate above and below the sheet leading to the development of chatter that appears as cross directional (CD) defects. Sheet defects from chatter will appear as multiple holes in the CD or develop a lace appearance. Coating defects can exhibit long CD marks that are visible when viewed with a strobe light. Under severe chatter conditions, the doctor blade will penetrate through the Yankee coating making direct contact with the dryer surface. If this occurs, potential damage to the dryer surface with the appearance of horizontal grooves on the metal surface can result. Once the dryer surface becomes damaged, it can only be repaired by taking the machine out of production and regrinding the dryer surface. Regrinding is a costly operation, because of production losses and cost of the procedure as well as degrading the dryer service lifetime due to reduction in wall thickness that negatively affects the vessel pressure rating. Therefore, it is imperative for manufacturers to closely monitor the process and identify when chatter is present.

Excessive vibration on the creping doctor blade, leading to chatter conditions, can originate through mechanical and operational or process conditions. Examples of mechanical vibration sources include press rolls, pumps, felts, Yankee cylinder bearings, etc., as well as dryer roundness deformation caused by thermal non-uniformities. Once a mechanical vibration source is identified, maintenance intervention to correct the problem often requires shutting down the equipment resulting in production loss. Conversely, operational practices or process conditions inducing excess vibration may include sheet moisture levels, coating chemistry, machine speed, basis weight, furnish, blade stick out and loading pressure, etc. can be attended to without interrupting production.

Regardless of the source, excess vibration experienced by the doctor blade can lead to chatter conditions affecting product quality, machine runnability, and asset value. Operators will often rely on audible sound changes or visual inspection (sheet quality or Yankee dryer surface) as the first indication that chatter is present. However, this approach is subjective and not reliable often resulting in detecting chatter after the condition has become severe, thus making corrective action steps more difficult. To improve the reliability and detection sensitivity for chatter detection, condition monitoring (CM) technology using piezoelectric and/or microphone sensor(s) can be used. CM has a long history in the paper industry, but mainly for use in bearing monitoring on rotating components. Examples of using CM on the creping doctor blade is limited and in these cases measurement analysis is made following traditional CM methods based on sensor signal level exceeding an alarm limit. In this approach, the system state is assessed from the sensor signal trend. A flat trend is considered a normal condition whereas an upward sloping trend indicates a wear condition, and a step change is considered a component failure. The dynamics of the Yankee dryer operation can produce large variations in the sensor signal, without reaching a chatter condition. As a result, data analysis becomes more complex compared to conventional CM based on wear and failure detection levels.

Previous attempts to address this problem include: Aurelio Alessadrini and Piero Pagani, *Chatter Marks: Origin, Evolution and Influence of the Creeping Doctors*, Ind. Carta vol. 41, no. 4, June 2003, pp 120-129, S. Archer, V. Grigoriev, G. Furman, L. Bonday, and W. Su, *Chatter and Soft Tissue Production: Process Driven Mechanisms, Tissue World Americas*, February-March 2009, pp 33-35, S. Zhang, J. Mathew, L. Ma, Y Sun, and A. Mathew, *Statistical condition monitoring based on vibration signals*, Proceedings VETOMAC-3 & ACISM-2004, pp. 1238-1243, New Delhi, India, M Fugate, H Sohn, and C. Farrar, *Vibration-based damage detection using statistical process control*, Mechanical Systems and Signal Processing, Vol. 15, Issue 4, July 2001, pp 707-721, H Sohn, C. Farrar, *Damage diagnosis using time series analysis of vibration signals*, Smart Materials and Structures, Vol 10, 2001, pp. 446-451, A. Heng, S. Zhang, A. Tan, and J Mathew, *Rotating machinery*

*prognostics: State of the art, challenges and opportunities*, Mechanical Systems and Signal Processing, 23, 2009, pp. 724-739, A, Messaoud, C. Weihs, and F. Hering, *Detection of chatter vibration in a drilling process using multivariate control charts*, Computational Statistics & Data Analysis, Vol. 52, 2008, 3208-3219, A. A., Junior, F. C. Lobato de Almeida, *Automatic faults diagnosis by application of neural network system and condition-based monitoring using vibration signals*, Proceedings of the 2008 IAJC-IJME International Conference, ISBM 978-1-60643-379-9, and A. G. Rehorn, J. Jiang, P. Orban, *State-of-the-art methods and results in tool condition monitoring: review*, Int J. Adv. Manuf Technol, 26, 2005, pp. 693-710. Unfortunately to date none of these attempts satisfactorily address the problems caused by chatter in doctor blades.

Thus there is clear need and utility for methods, compositions, and apparatuses for the detection and prevention of chatter in doctor blades. The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 CFR .sctn.1.56 (a) exists.

BRIEF SUMMARY OF THE INVENTION

At least one embodiment of the invention is directed towards a method of detecting and addressing chatter from Yankee dryer doctor blades used in the creping process, cleaning, and/or cut-off operations. The method comprises the steps of:

over a period of time, with an sensor constructed and arranged to measure the frequencies and amplitudes of vibrations in a doctor blade as it crepes a paper product, measuring the frequencies and amplitudes of the vibrations indexed by time, collecting the measurements into a time waveform, converting the waveform using a fast-Fourier transform having a frequency spectrum which includes distinct vibration bands, correlating characteristics of the vibration bands with performance properties of the doctor blade and to define a baseline of acceptable vibration bands, predicting from the correlated characteristics the degree of deviation from the baseline of acceptable vibration bands associated with doctor blade chatter, and outputting when a data point on a vibration band exceeds the degree of deviation excessive chatter has occurred.

The sensor may be an accelerometer and/or a piezoelectric accelerometer. The measurements may be analyzed and modeled by a data processing device constructed and arranged to utilize one process selected from the group consisting of: RMS data trending, neural network techniques, multiple regression analysis, AR, ARMAX, partial least squares, and any combination thereof. At least one of the correlations may be determined by comparing characteristics of the vibration bands with blade age. The measurements may be analyzed and modeled by a data processing device constructed and arranged to utilize RMS data trending and where the determination is made at least in part by noting that the slope in a saw tooth shaped vibration band continuously increases over time with the same blade and becomes discontinuous when the blade is changed.

The method may further comprise the step of defining a deviation from the baseline due to chatter to only occur when a deviation exceeds the mean and standard deviation to of the baseline due to both an increase in magnitude and a duration of that increase greater than the mean duration of all data spikes in the waveform. The method may further comprise the steps of pre-determining the slope at which the blade is too old to be desired for use and replacing the blade when such a slope manifests on the waveform.

At least one of the correlations may be determined by comparing characteristics of the vibration bands with one factor selected from: track bearing, balance, dryer lubricity, dust levels, moisture levels, temperature, felt age, grade, furnish composition, coating chemistry, cleaning blade status (on or off), machine speed, external source vibrations, external pressure sources, and any combination thereof. The range of characteristics of the vibration bands caused by the factor may be so broad that the sensor must be capable of detecting frequency bandwidth spanning four orders of magnitude. In at least one embodiment the sensor only indirectly measures vibrations of the doctor blade because it is engaged not to the blade itself but to a blade holder which is engaged to and provides more rigid support to the blade but which does not dampen the vibration to such an extent that an accurate measurement cannot be taken. The measurements may be taken synchronously and/or asynchronously. The output may be an alarm.

Additional features and advantages are described herein, and will be apparent from, the following Detailed Description.

DETAILED DESCRIPTION OF THE INVENTION

Figure 1:
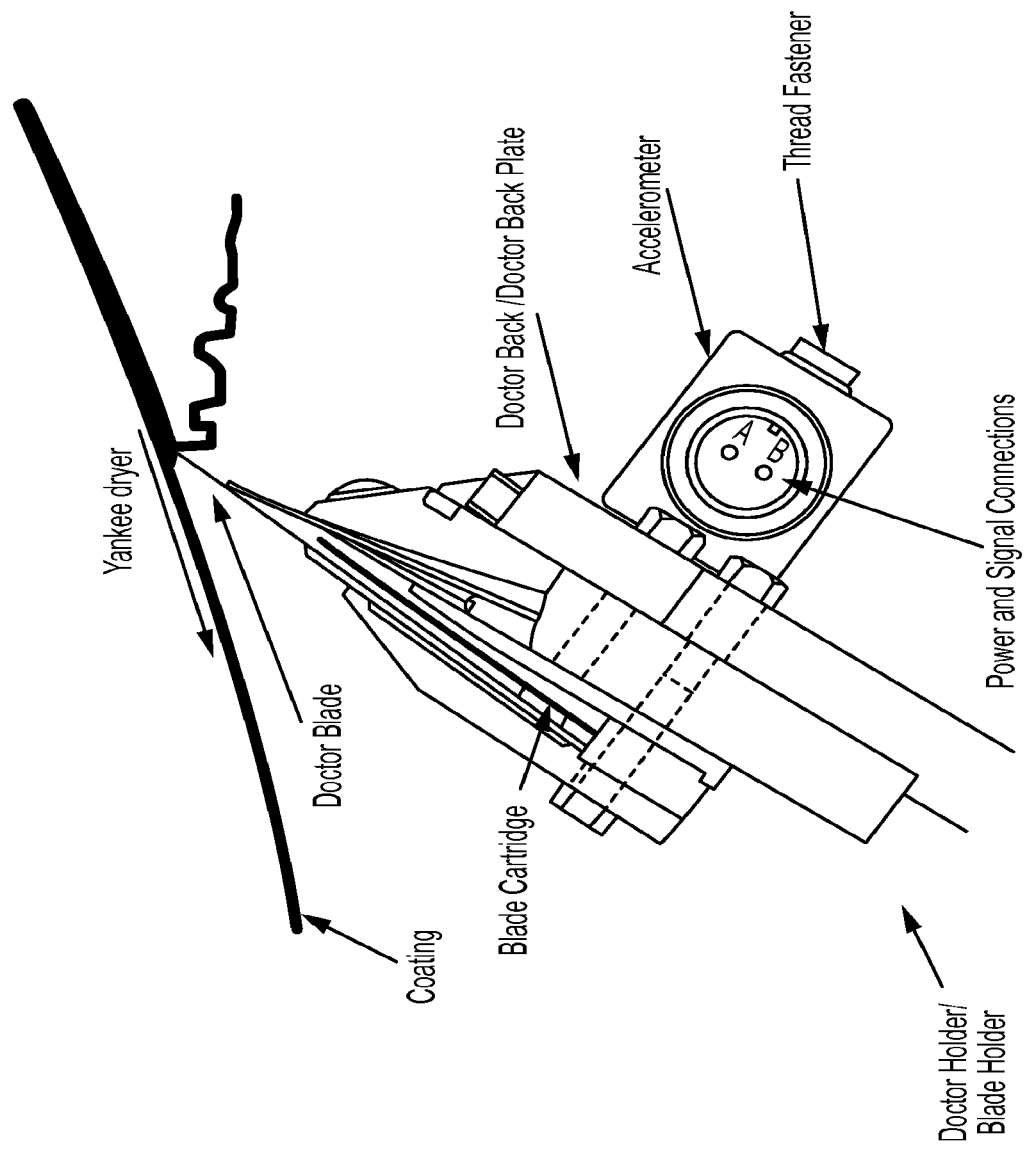
FIG. 1 illustrates a side view of an embodiment of the invention utilizing an accelerometer sensor measuring the operation of a doctor blade.

The following definitions are provided to determine how terms used in this application, and in particular how the claims, are to be construed. The organization of the definitions is for convenience only and is not intended to limit any of the definitions to any particular category.

"Bevel" or "bevel surface" as used herein refers to the portion of the blade that forms the surface between the leading edge of the blade and the trailing side of the blade and is typically the "working surface" of the blade.

"Bulk" means the inverse of the density of a tissue paper web and is usually expressed in units of cm.sup.3/g. It is another important part of real and perceived performance of tissue paper webs. Enhancements in bulk generally add to the clothlike, absorbent perception. A portion of the bulk of a tissue paper web is imparted by creping.

"Cross Machine Direction" or "CD" means the direction perpendicular to the machine direction in the same plane of the fibrous structure and/or fibrous structure product comprising the fibrous structure.

"Doctor Blade" means a blade that is disposed adjacent to another piece of equipment such that the doctor blade can help remove from that piece of equipment a material that is disposed thereon. Doctor blades are commonly used in many different industries for many different purposes, such as, for example, their use to help remove material from a piece of equipment during a process. Examples of materials include, but are not limited to, tissue webs, paper webs, glue, residual buildup, pitch, and combinations thereof. Examples of equipment include, but are not limited to, drums, plates, Yankee dryers, and rolls. Doctor blades are commonly used in papermaking, nonwovens manufacture, the tobacco industry, and in printing, coating and adhesives processes. In certain instances, doctor blades are referred to by names that reflect at least one of the purposes for which the blade is being used.

"Fiber" means an elongate particulate having an apparent length greatly exceeding its apparent width. More specifically, and as used herein, fiber refers to such fibers suitable for a papermaking process.

"Highly polished" means surface that has been processed by a sequential progression from relatively rough grit to fine grit with suitable lubrication and is highly planar and substantially free of defects. Such sequential progression will be referred to herein as a "step polishing process."

"Machine Direction" or "MD" means the direction parallel to the flow of the fibrous structure through the papermaking machine and/or product manufacturing equipment.

"Paper product" means any formed, fibrous structure products, traditionally, but not necessarily, comprising cellulose fibers. In one embodiment, the paper products of the present invention include tissue-towel paper products. Non-limiting examples of tissue-towel paper products include toweling, facial tissue, bath tissue, table napkins, and the like.

"Sheet control" as used herein, refers to the lack of vibrations, turbulence, edge flipping, flutter, or weaving of the web that result in a loss of control at higher speeds.

"Softness" means the tactile sensation perceived by the consumer as he/she holds a particular product, rubs it across his/her skin, or crumples it within his/her hand. This tactile sensation is provided by a combination of several physical properties. One of the most important physical properties related to softness is generally considered by those skilled in the art to be the stiffness of the paper web from which the product is made. Stiffness, in turn, is usually considered to be directly dependent on the strength of the web.

"Strength" means the ability of the product, and its constituent webs, to maintain physical integrity and to resist tearing, bursting, and shredding under use conditions.

"Tissue Paper Web", "paper web", "web", "paper sheet", "tissue paper", "tissue product", and "paper product" are all used interchangeably and mean sheets of paper made by a process comprising the steps of forming an aqueous, papermaking furnish, depositing this furnish on a foraminous surface, such as a Fourdrinier wire, and removing a portion of the water from the furnish (e.g., by gravity or vacuum-assisted drainage), forming an embryonic web, and in conventional tissue making processes transferring the embryonic web from the forming surface to a carrier fabric or felt, and then to the Yankee dryer, or directly to the Yankee dryer from the forming surface. Alternatively in TAD tissue making processes, the embryonic web may be transferred to another fabric or surface traveling at a lower speed than the forming surface. The web is then transferred to a fabric upon which it is through air dried to a dryness typically between 10 to 50%, and finally to a Yankee dryer for final drying and creping, after which it is wound upon a reel.

"Water Soluble" means materials that are soluble in water to at least 3%, by weight, at 25 degrees C.

In the event that the above definitions or a description stated elsewhere in this application is inconsistent with a meaning (explicit or implicit) which is commonly used, in a dictionary, or stated in a source incorporated by reference into this application, the application and the claim terms in particular are understood to be construed according to the definition or description in this application, and not according to the common definition, dictionary definition, or the definition that was incorporated by reference. In light of the above, in the event that a term can only be understood if it is construed by a dictionary, if the term is defined by the Kirk-Othmer Encyclopedia of Chemical Technology, 5th Edition, (2005), (Published by Wiley, John & Sons, Inc.) this definition shall control how the term is to be defined in the claims.

In at least one embodiment of the invention, a method detects the onset of creping doctor blade chatter. This method, by alerting machine operators that blade chatter conditions are imminent, allows operators to take corrective action avoiding runnability problems and preventing damage to the Yankee dryer surface. The method utilizes signal analysis using at least one piezoelectric accelerometer operated near the doctor blade holder. In at least one embodiment the analysis method differs from conventional CM techniques by using a time-integrated approach. As a first level approach, the signal is tracked based on both intensity above an alarm limit and duration. This allows accounting for strong vibration, but short duration, as well as weaker vibration over long periods. Enhanced monitoring is described by extending this method to predictive models using process input data, wavelet analysis for spatially resolved MD high vibration regions on the dryer surface, and trend slope analysis to predict the onset of an encroaching alarm condition. In all cases, the Yankee dryer exposure to excess vibration is accounted for by tracking the accumulated time integrated value, thus providing an historical record to help in maintenance scheduling.

In at least one embodiment the method comprises the steps of detecting directly or indirectly the vibration of the crepe doctor blade. In at least one embodiment the sensor technology is robust enough to operate in harsh environmental conditions. The conditions include one or more of high dust levels, high moisture levels and temperatures >125.degree.C. In addition, the geometric constraints around the creping operation may require a compact sensor footprint. Furthermore, in some circumstances the sensor must be capable of detecting a frequency bandwidth spanning four orders of magnitude (for example 10 Hz to 20 kHz).

In at least one embodiment the piezoelectric accelerometer used is a typical commercially available off-the-shelf sensor that meets these criteria. Industrial accelerometers such as the SKF model CM2207 are hermetically sealed and hardened with an acceptable footprint (54.times.30 mm) for mounting on or near the creping doctor blade holder. In at least one embodiment the accelerometer is directly mounted on the crepe doctor blade to monitor the blade vibration as it is in contact with the coating and surface of the Yankee dryer. However, direct mounting on the doctor blade poses additional challenges with greater geometric constraints, higher temperatures, and limited blade service life requiring frequent (a few hours to 24 hrs, depending on the process and blade composition) blade changes. Therefore, in at least one embodiment the sensor mounting is positioned on the doctor blade holder. This provides an effective alternative since the blade holder is in close proximity to and in contact with the doctor blade and is itself stationary.

An illustration of one possible arrangement for mounting an accelerometer on a doctor holder is shown in FIG. 1. In the blade holder, the doctor back plate provides a flat rigid surface for sensor mounting. In at least one embodiment the sensor mounting method is with a tapped hole on the doctor holder and thread fastener through the center of the accelerometer sensor. Adhesive mounting can also be used but at the sacrifice of higher frequency detection. Other blade holder designs used are the ladder back and super crepe as well as all other means known in the art and their equivalents. Regardless of the blade holder design, sensor mounting close to the doctor blade on a structurally rigid support with minimum dampening is the preferred method. Sensor location along the doctor back CD is dependent on the machine operation. If possible, the sensor should be located inside the sheet edge and preferably, multiple sensors are used to monitor different zones in the CD.

Figure 2:
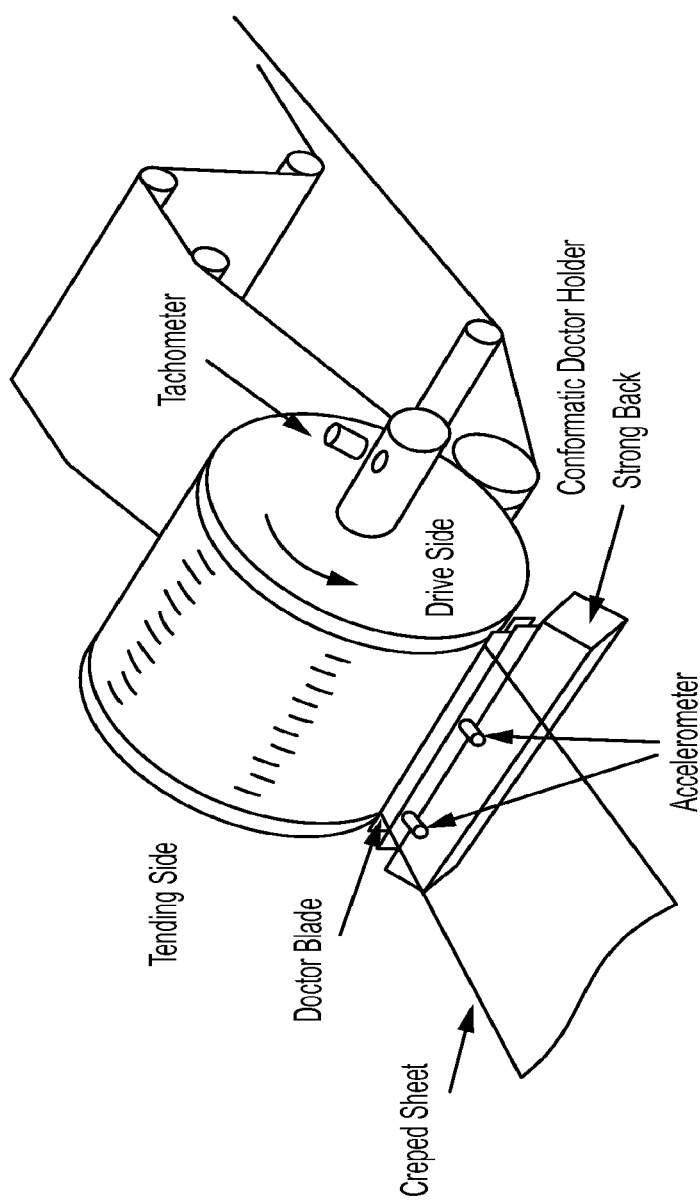
FIG. 2 illustrates a perspective view of an embodiment of the invention utilizing two accelerometer sensors to measure the operation of a doctor blade.

Referring now to FIG. 2 there is shown an illustration of accelerometer mounting inside of the sheet by the tending and drive sides on a Yankee dryer. In this case, sensors to mounted near the drive and tending side sheet edge allow detecting differences in vibration frequencies and amplitudes between the sides. Therefore, using a minimum of two sensors positioned equal distances from the tending and drive side edge is the preferred approach. In principle, a single sensor could also be used, but at the sacrifice of sensitivity and monitoring the side-to-side variation.

In at least one embodiment signal transmission from the sensors mounted near the creping doctor blade is made through hard wire cable or wireless communication to a vibration data acquisition unit, e.g., the SKF IMX-S on-line multilog system or any equivalent thereof. Data sent by the sensor can be raw, e.g., waveform, or processed through a microprocessor integrated into the sensor or signal transmission line. The data acquisition system processes the sensor data and displays the results and alarm status as well as a providing a means to achieve and retrieve data. In at least one embodiment, the data acquisition system can monitor other process variables such as the machine speed and can use a tachometer for synchronous data collection.

Data collected from the acquisition system can also be routed through Ethernet or wireless to a centralized location (within a corporation or external) where data from several monitoring systems can be further analyzed. Compiling the data from several sites allows for the calculation of aggregate performance properties and relative rankings of the blade chatter levels.

Process variables for the Yankee dryer unit operation are dynamic with varying time scales from minutes to days. Process variables such as creping blade age, felt age, grade, furnish, coating chemistry, cleaning blade status (on or off), machine speed, etc., all contribute to the vibration signature observed on the creping doctor blade. In addition, vibration originating from other sources such as fan pump, Yankee dryer bearings, pressure roll, overhead crane, etc. can also propagate through the process structure to the crepe blade. The aggregate of the vibration sources results in the overall vibration signature detected by the sensor. For a piezoelectric accelerometer sensor, the vibration signature monitored is a time waveform that can be collected synchronous or asynchronous relative to the Yankee dryer rotation. Taking a fast-Fourier transform (FFT) of the waveform gives a frequency spectrum that provides unique vibration frequencies and/or bands. Further data reduction is made by extracting the root-mean-square (RMS) from the FFT power spectral density to get an overall and/or bandwidth vibration magnitude value to trend over time.

Figure 3A:
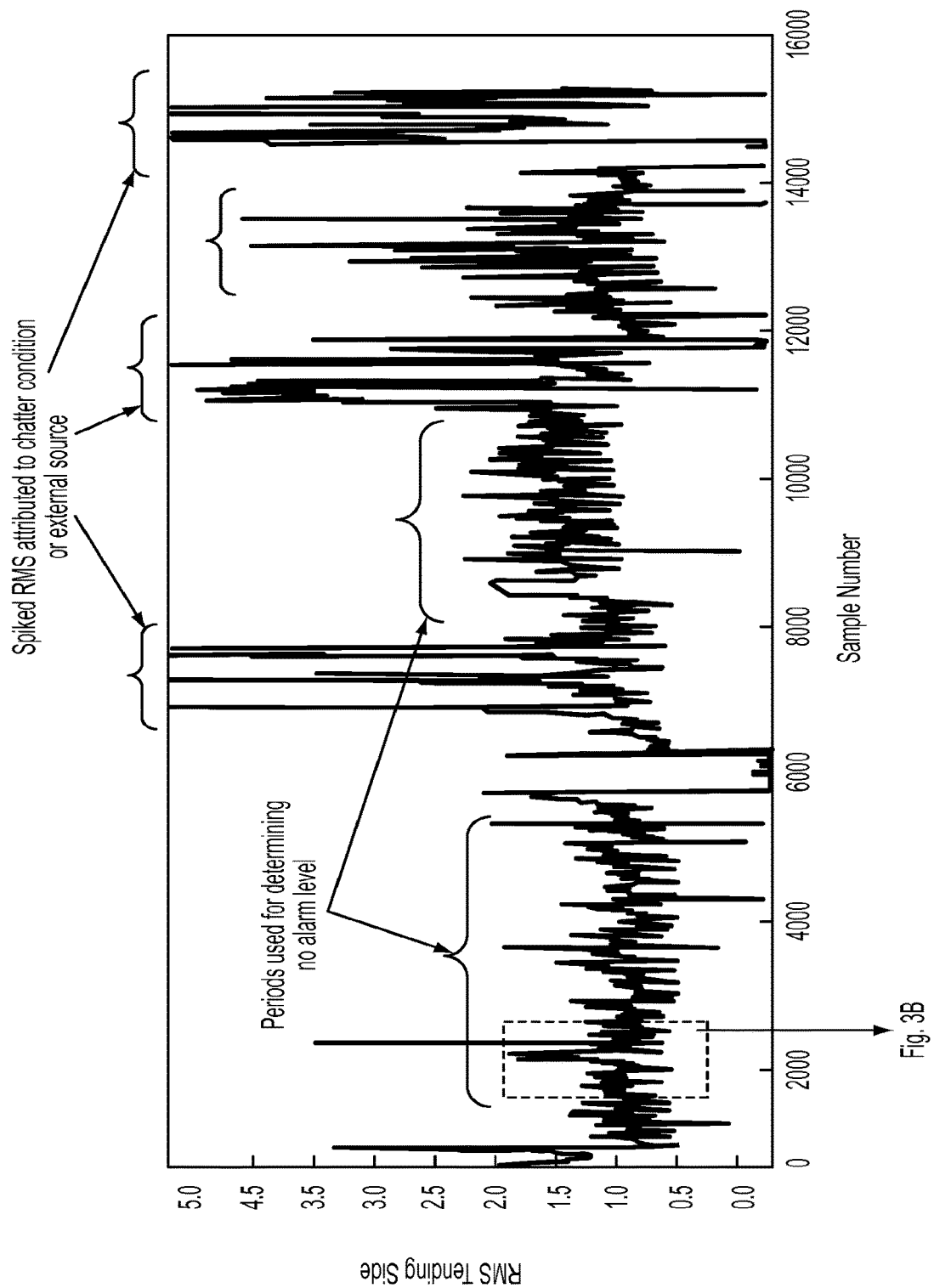
FIG. 3A is a graph of an RMS trend from an accelerometer utilizing the invention.
Figure 3B:
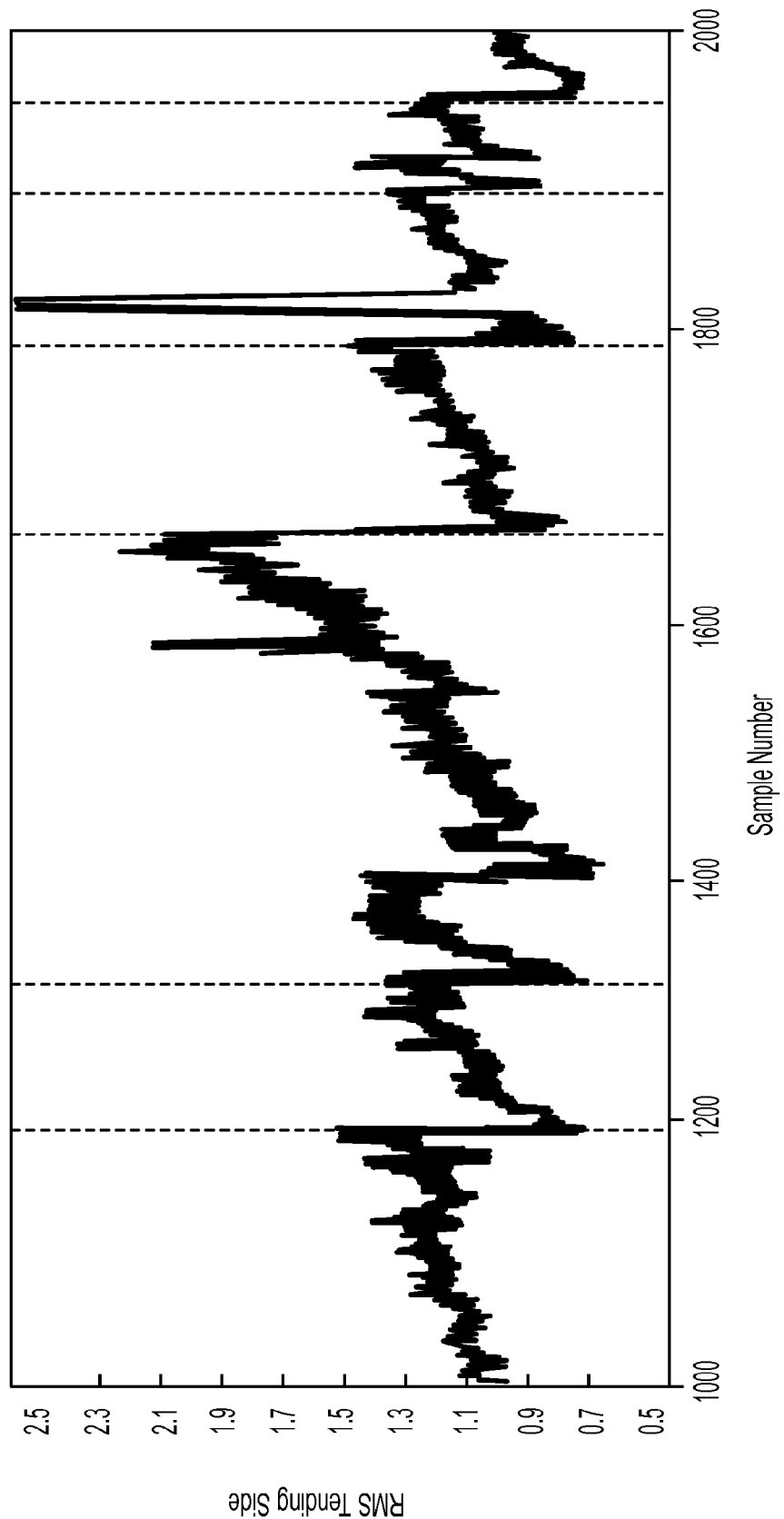
FIG. 3B is a graph of an expanded view of an RMS trend from an accelerometer utilizing the invention.

The RMS trend from an accelerometer mounted on the creping doctor blade holder will show natural variations under normal operating conditions because of the process dynamics. The complexity and multiple interactions from the different vibration sources makes identifying specific process variables contributing to a unique vibration frequency or band a difficult task. However, some general features such as blade age are clearly observed in the RMS trend as a saw tooth pattern. Installing a new blade will reduce the RMS by improved efficiency (reduced drag) in cutting through the coating and removing the sheet. As the blade degrades over time, the drag will increase resulting in the RMS increasing. To illustrate this point, FIG. 3 shows an RMS trend for 0-10 kHz bandwidth data collected over 11 days. The trend is composed of a natural process variation baseline associated with the creping doctor blade age as well as periods where the RMS value spikes relative to the baseline.

Different features on FIG. 3 are highlighted and a zoomed area shows the effect of the creping blade age on the RMS trend (vertical markers indicate periods where a blade change occurred). Periods where the RMS levels spike can potentially lead to degradation of the coating and/or the dryer surface. The vibration source associated with these spikes is not always obvious, and often requires further investigation of the process and operating (human and mechanical) conditions. Degradation of the Yankee coating or dryer surface may occur from a single RMS spike event or a cumulative effect over time. Therefore, minimizing the frequency and amplitude of the RMS excursions above the natural baseline is a best practice scenario for maintaining runnability and asset protection.

As a first level for chatter monitoring, the state of the creping doctor blade vibration is tracked by using an nσ alarm based on the mean and standard deviation (σ) of RMS trend data that excludes the spiked periods and no visible chatter is present in the coating or dryer surface. Alarming sensitivity is based on the user selected number of standard deviations from the mean. Alarming (real-time) is based on the RMS level or RMS level and time duration. For just RMS alarming, an alarm signal (visual, audible or combination) is sent to the operator and stored in a database when the RMS value is greater than the nσ alarm level setting. Different states of alarming can be selected by using multiple nσ settings. For example, a 2σ alarm level can be a warning alarm alerting the operator the RMS value is trending upward, but not yet reaching a critical state. If the RMS value continues to trend upward past the 3σ alarm setting then a critical alarm can be sent to the operator. This method of alarming is commonly found in commercial condition monitoring systems used in predictive maintenance on rotating machinery. In this application, condition monitoring tracks bearing, balance, and overall integrity health on machinery. As the bearing wears the RMS trend from a sensor (typically an accelerometer mounted near the bearing of the rotating shaft) will gradually increase indicating that bearing maintenance such as replacement or lubrication is needed. If left unattended the RMS level would remain at a high level or continue to climb upward.

Unlike traditional condition health monitoring, the dynamics of the creping process can result in large RMS variations without developing chatter. Therefore, a transient RMS spike above an nσ alarm level does not necessarily warrant an alarm event. However, as the duration of the RMS value above the alarm setting increases, the probability of developing chatter increases. In this alarming mode, the alarm signal strength (alarm*) is a function of both the RMS value>nσ alarm level (RMS$^+$) and the duration the RMS$^+$ signal remains above the alarm level. The expression for the alarm* signal is given by $$\text{Alarm}^*(RMS,t) = (w_{RMS} RMS^+)(w_t t)$$

where $W_{RMS}$ and $w_t$ are weighting parameters or functions, t is the time above the alarm level, and RMS$^+$ is the difference between the RMS signal and the nσ alarm value. Trending the time integrated alarm signal will show variations >0 for conditions when the RMS level is above the nσ set-point and increases with time. This method addresses both short duration high RMS values as well as RMS values that remain slightly higher than the alarm level for long periods.

The second mode of alarming is based on the accumulative effect of alarm* over time and can be trended continuously as well as reported daily, weekly, monthly, or yearly. The accumulated alarm*$_{Acc}$ is given by $$\text{Alarm}^*_{Acc} = \Sigma \text{ Log}(\text{Alarm}^*)$$

and represents the total excess vibration the Yankee dryer is exposed to over time. Minimizing the frequency, duration, and amplitude of the alarm*$_{Acc}$ will reduce the Yankee exposure to critical vibration levels thereby minimizing maintenance and extending the asset service life. Trending the alarm*$_{Acc}$ is useful for evaluating and predicting different maintenance levels for the Yankee dryer ranging from simple inspection to surface reconditioning. The accumulated alarm information also helps to identify differences in operating procedures, e.g., between workers shifts, grades manufactured, furnish, etc., where the vibration levels may trend abnormally high.

Figure 4:
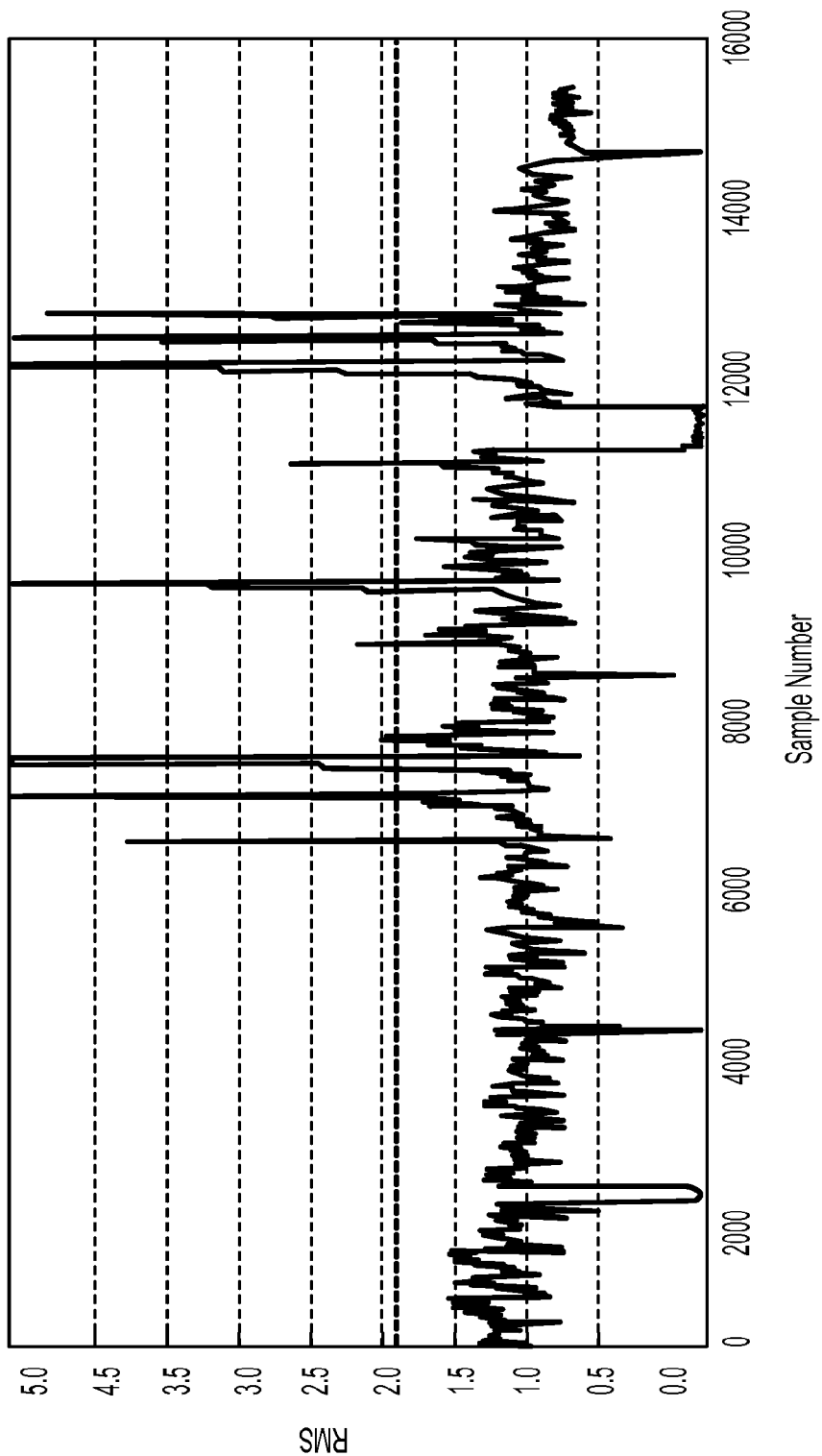
FIG. 4 is a graph of an RMS trend including an alarm set point from an accelerometer utilizing the invention.
Figure 5:
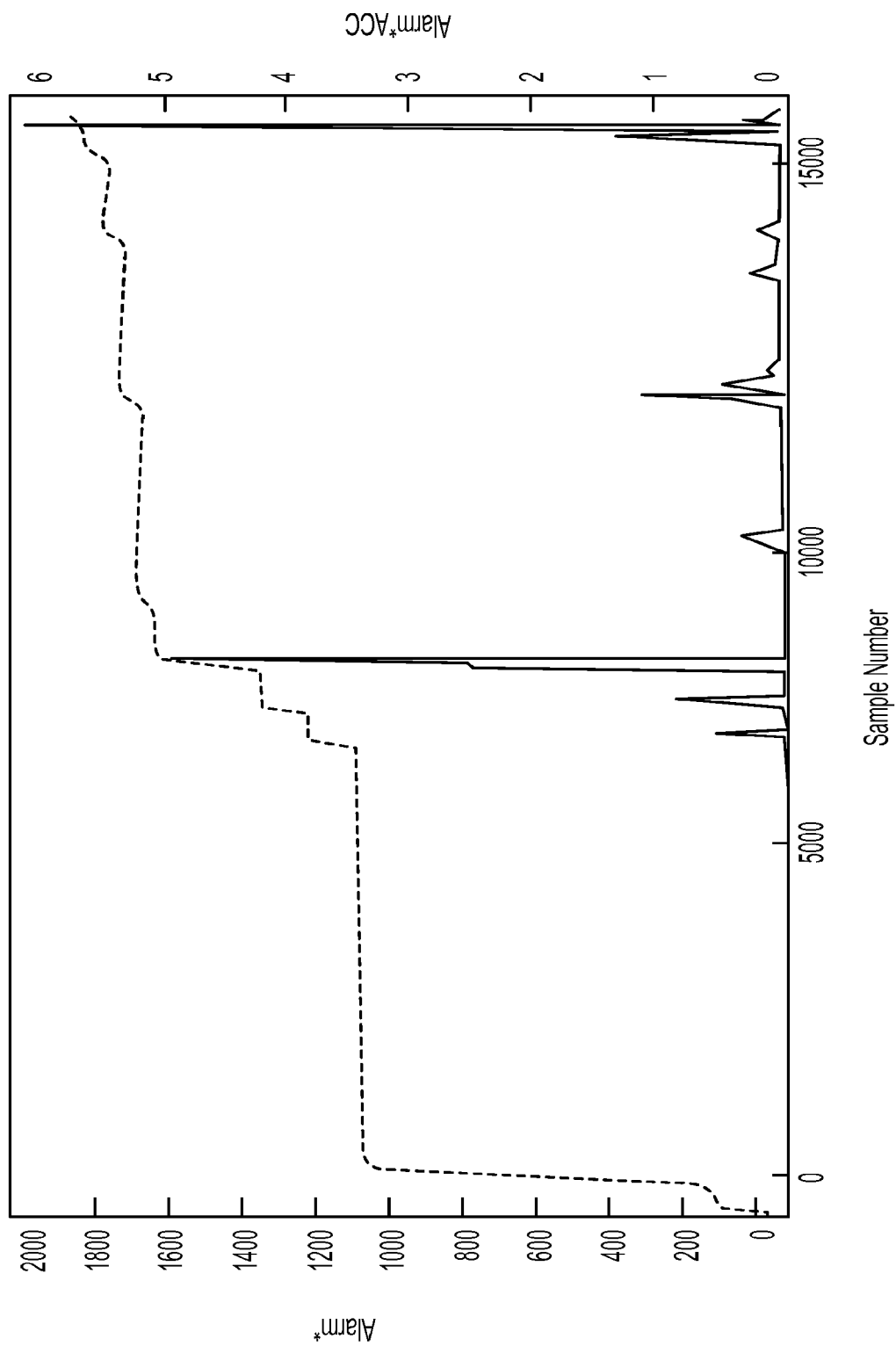
FIG. 5 is a graph of a time integrated alarm and accumulated alarm from RMS data from an accelerometer utilizing the invention.

An example using this alarming strategy for the RMS vibration data collected over 11 days is shown in FIG. 4 for a 1.0 minute sampling rate. FIG. 4 shows the measured RMS data collected with a 3σ alarm level determined from an independent training set of data. The plot shows the historical RMS trend recorded with the 3σ alarm level (dashed line). FIG. 5 shows the resulting time integrated alarm* value using unit weighting values. Under normal operating conditions alarm*=0.0, since the RMS value is below the 3σ alarm level. Also shown on FIG. 5 is the accumulated alarm*$_{Acc}$ value to track the total excess vibration the dryer surface has been exposed to over the 11 day period.

In at least one embodiment the alarming method also involves a predictive model that reduces or removes the process dynamics contributing to the measured vibration. The benefit of using a predictive model is improved alarming sensitivity and reduction in false positive alarms. Numerous model building techniques such as neural network (NN), multiple regression, autoregressive (AR), autoregressive moving average with exogenous terms (ARMAX), state-space, partial least squares, and any combination thereof, can be used to develop a predictive model based on the waveform, frequency spectrum, or RMS trend data. Ideally, model construction begins by collecting process bump testing data to develop cause-and-effect relationships. However, bump testing is generally restricted to a limited range of process changes to minimize quality and production loses. To address this issue data collection over long periods is required to capture process changes for model tuning. Alternatively, continuous tuning (learning) using adaptive algorithms can be used to update the model. Using a predictive model requires process input data that can be collected from the distributed control system or monitored directly with the vibration data acquisition system. In either case, the process data collected is used as a model input.

Figure 6:
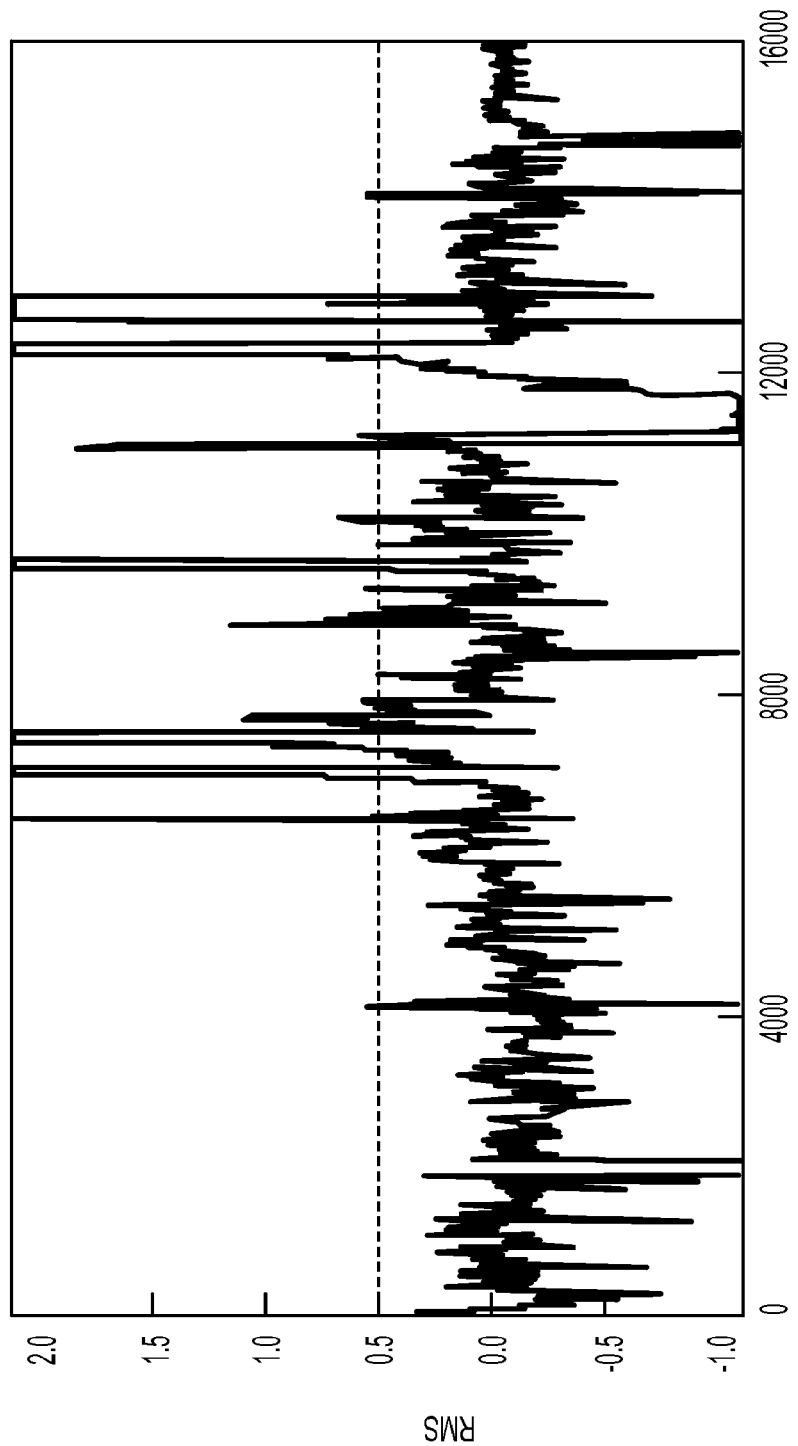
FIG. 6 is a graph of RMS residuals from a predictive model utilizing data obtained from an accelerometer utilizing the invention.

An example illustrating a predictive NN model of the RMS trend from FIG. 4 based on a process model with 25 input variables is shown in FIG. 6 as a plot of the residuals (difference between the measured and predicted value). In this example, the creping blade age dependency is modeled by applying a transformation on the blade change data that is reported as the time of the event to force the model to have similar behavior. The transformation uses a fixed slope based on the average obtained from the RMS trend measurements over the life of a blade. Large residuals represent a process condition not captured by data in the model building step. The large residuals may or may not be an actual chatter condition, but are an indication that excess vibration has propagated to the creping doctor blade.

Figure 7A:
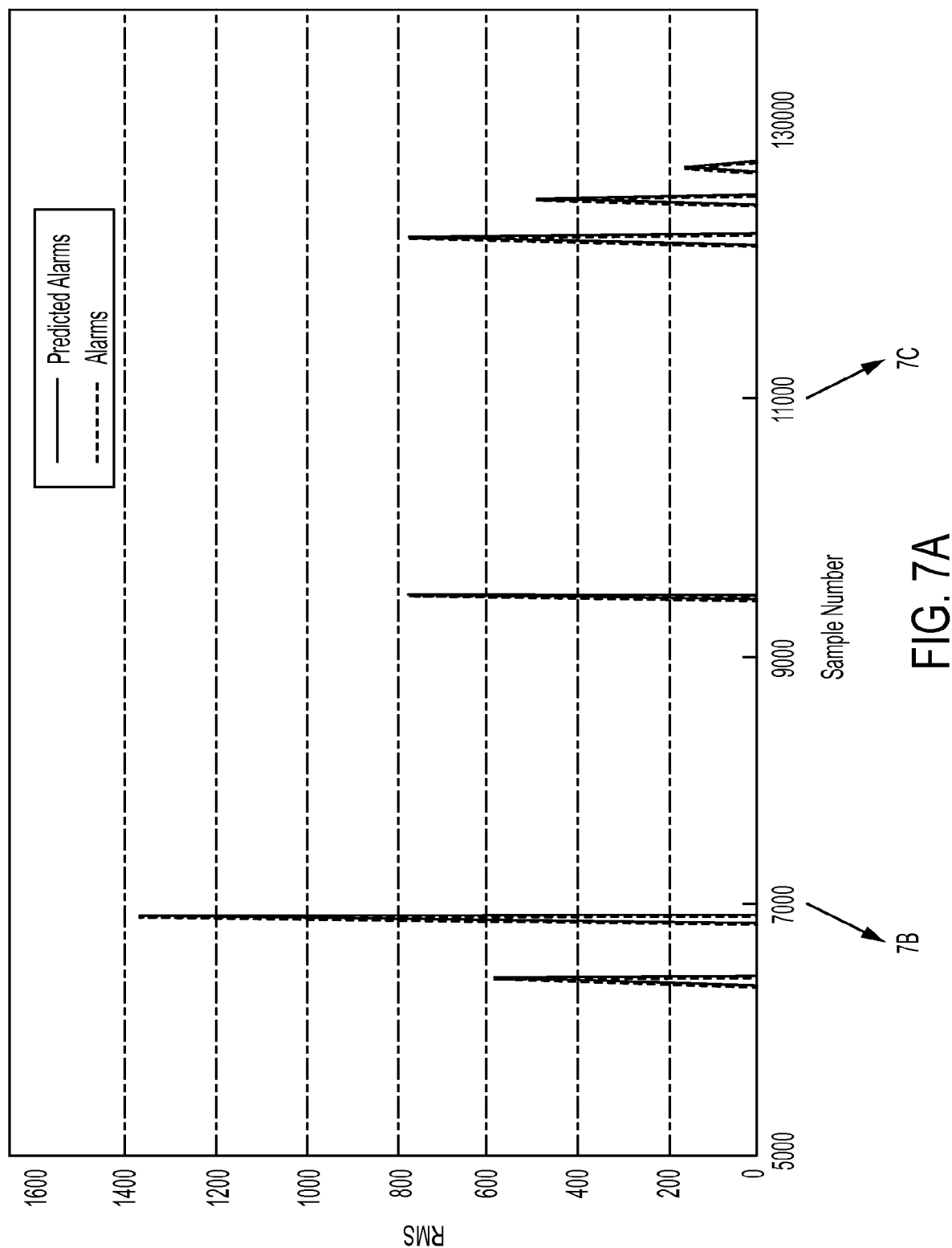
FIGS. 7A-7C show a group of graphs showing the advantage of predictive modeling for early warning chatter detection and to prevent false positive alarms.
Figure 7B:
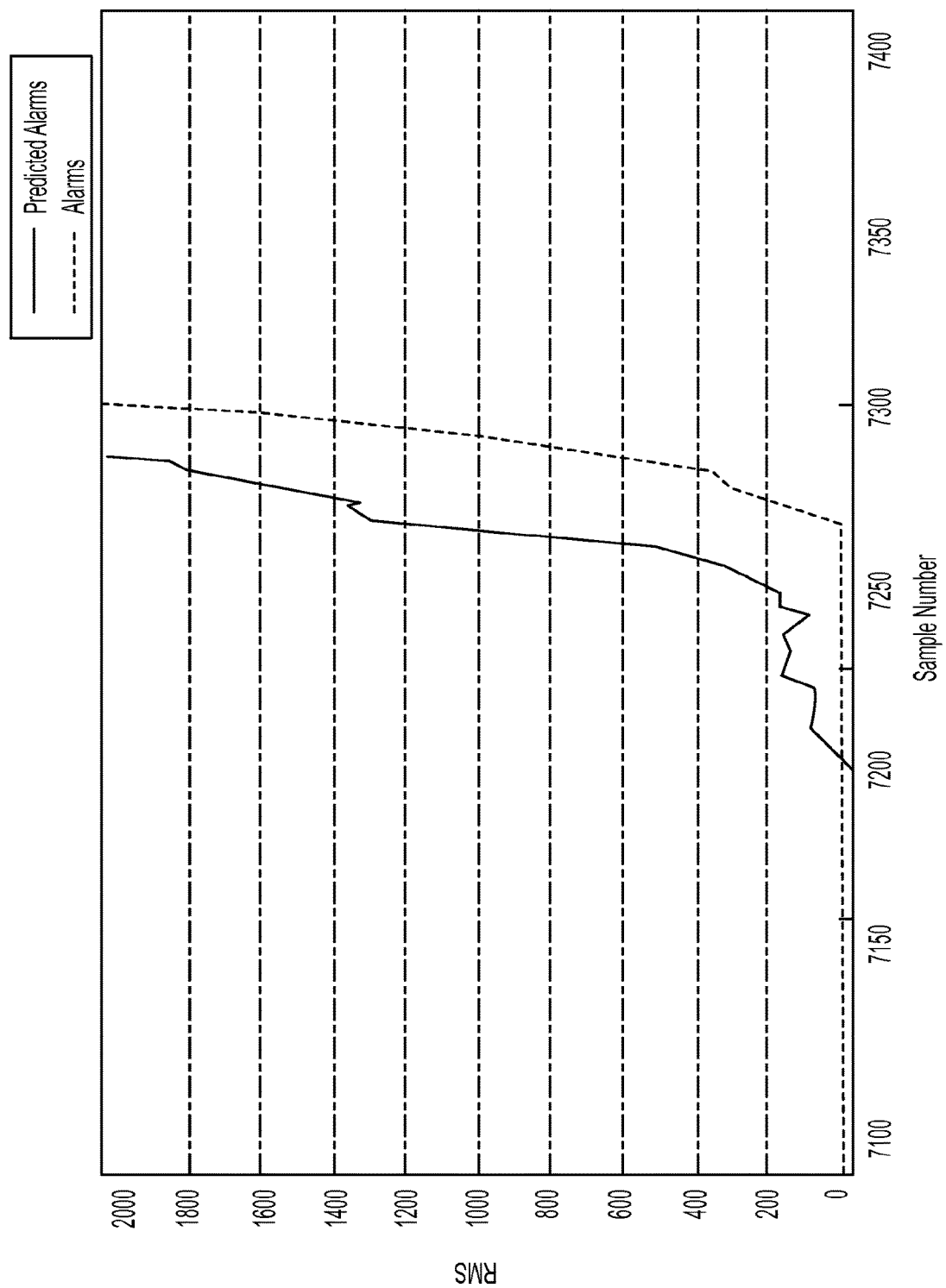
Figure 7C:
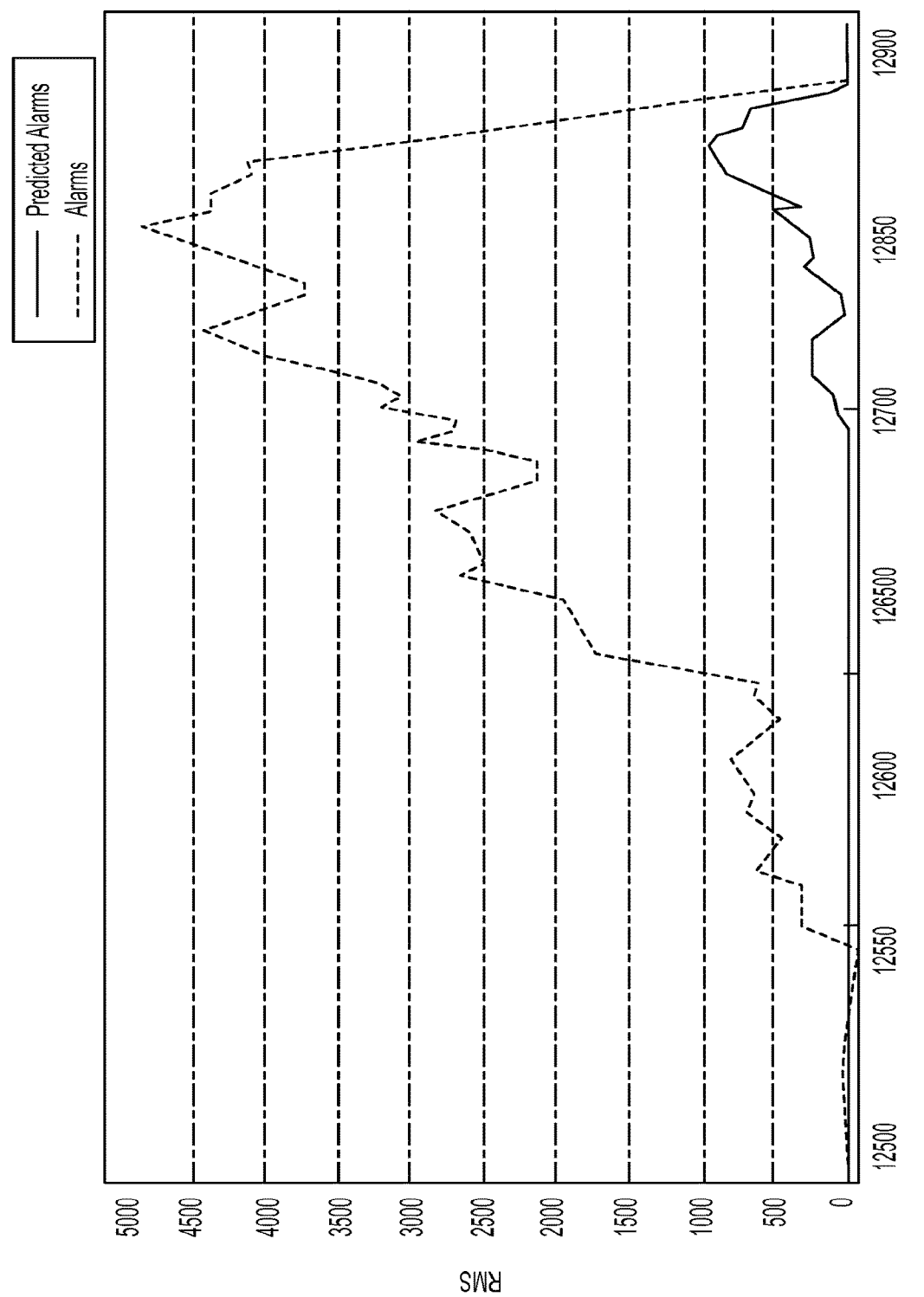

The advantages of using the predictive model for alarming is shown in FIG. 7A for time integrated alarming. FIGS. 7B and 7C show zoomed areas of FIG. 7A, illustrating two different cases. FIG. 7B shows a zoomed portion of the left hand side of FIG. 7A, and shows the predicted (residual) alarm* value appearing before the alarm* value from FIG. 4 data. In this case, the predicted alarm* value occurs almost 60 minutes before the standard alarm* value. The early alarming results from lower 3σ alarm level. FIG. 7C shows the right hand side of FIG. 7A, and shows just the opposite effect with alarm* occurring first. In this case, the NN model accounts for the contribution to RMS from the process conditions and reduces or removes the occurrence of a false positive alarm condition.

Figure 8:
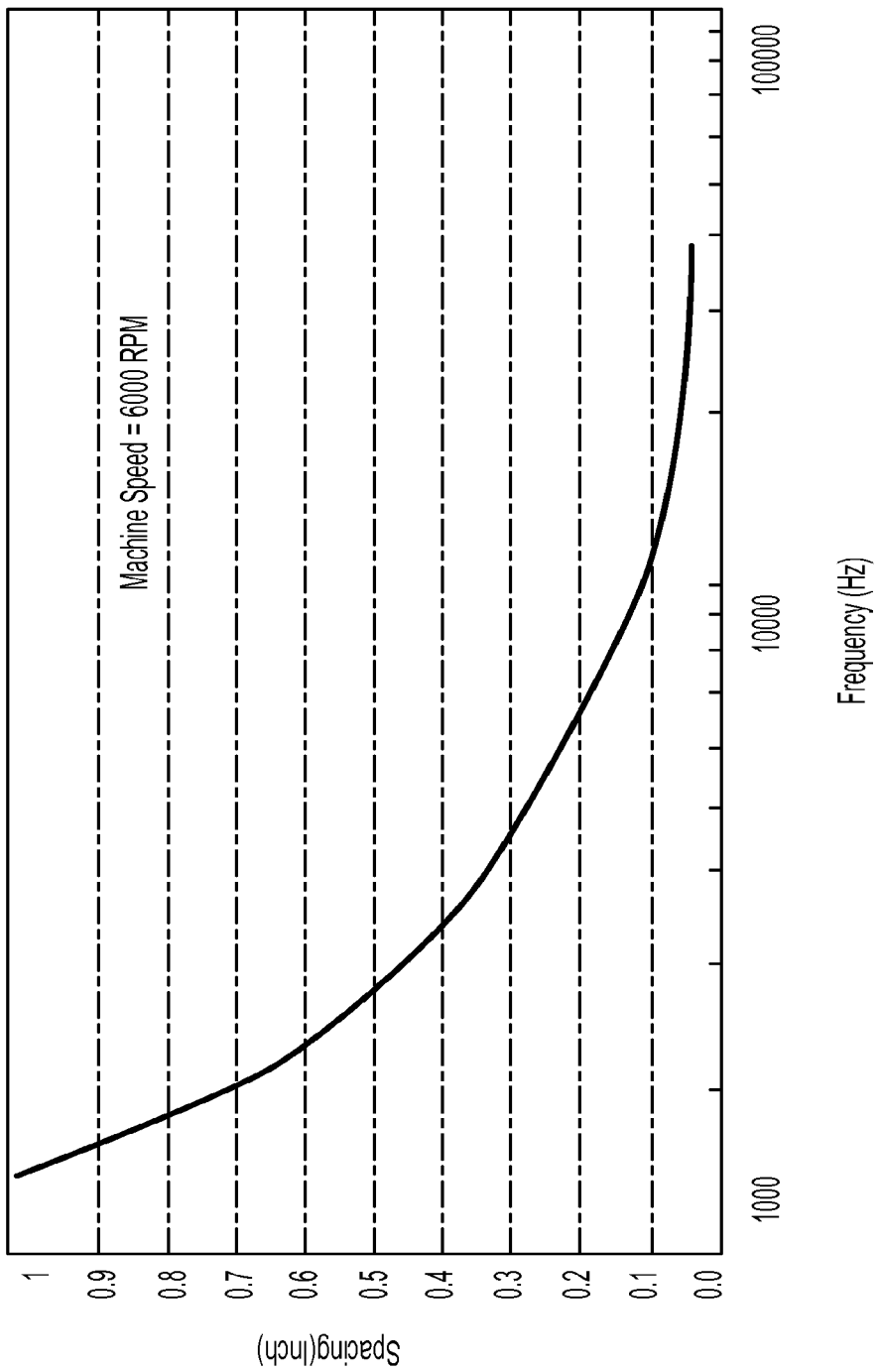
FIG. 8 is a graph of estimated vibration frequency for different chatter mark spacings on a Yankee dryer.

In at least one embodiment of the invention, a vibration frequency or band is monitored with alarming based on simple nσ alarm level or time integrated alarming. Unlike many of the mechanical vibration sources that occur at frequencies <500 Hz, chatter appears at higher frequencies. In cases where chatter is visible in the coating or dryer surface an estimate of the frequency range is made by measuring the spacing between the chatter marks and knowing the dryer speed. As the chatter mark spacing decreases the chatter frequency increases as shown in FIG. 8 for a fixed 6000 FPM machine speed. Even at a chatter mark spacing of 1 inch the estimated vibration frequency at this machine speed is >1000 Hz. In the development of chatter by the stick-slip mechanism (S. Archer et. al., Tissue World Americas 2008) visible chatter mark spacing is typically much less than an inch. Therefore, high frequency band monitoring can improve the measurement sensitivity to detect chatter. The sensitivity gain is obtained by focusing on smaller spectral regions compared to monitoring the overall RMS that can be affected by low frequency non-chatter events, e.g., the fan pump. In addition, changes in a narrow spectral region may be attenuated in the overall RMS value because of averaging with the surrounding spectral features.

Figure 9:
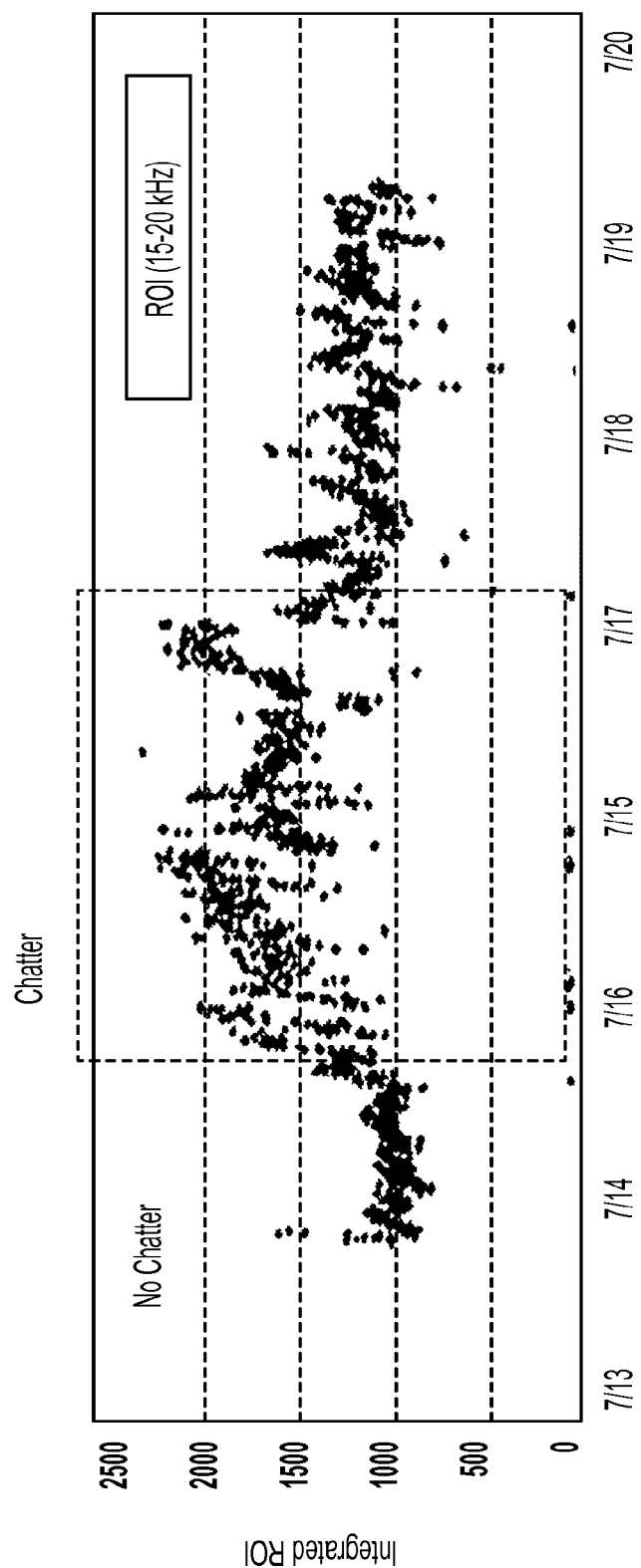
FIG. 9 is a trend graph of an integrated frequency band (15-20 kHz) with and without chatter visible in the coating.
Figure 10A:
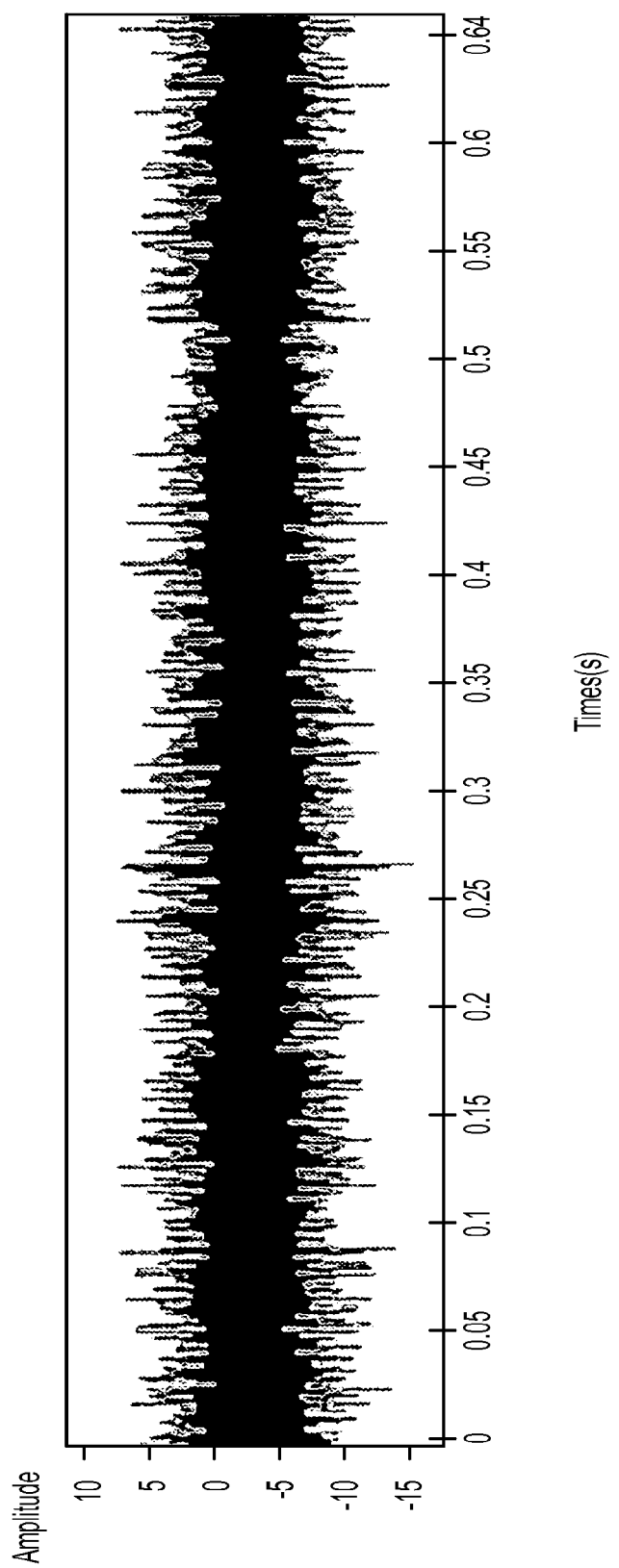
FIG. 10A is the raw sensor data for one Yankee cylinder revolution from an accelerometer utilizing the invention.
Figure 10B:
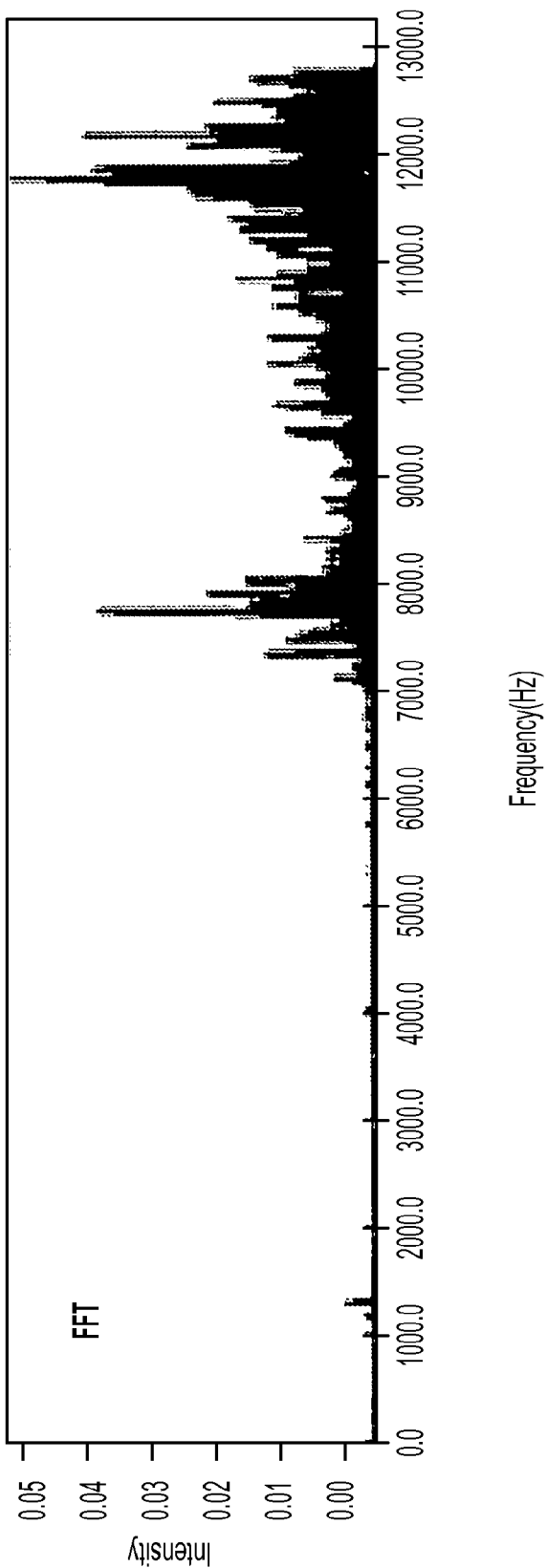
FIG. 10B is a fast Fourier transformation (FFT) of the data in FIG. 10A.
Figure 10C:
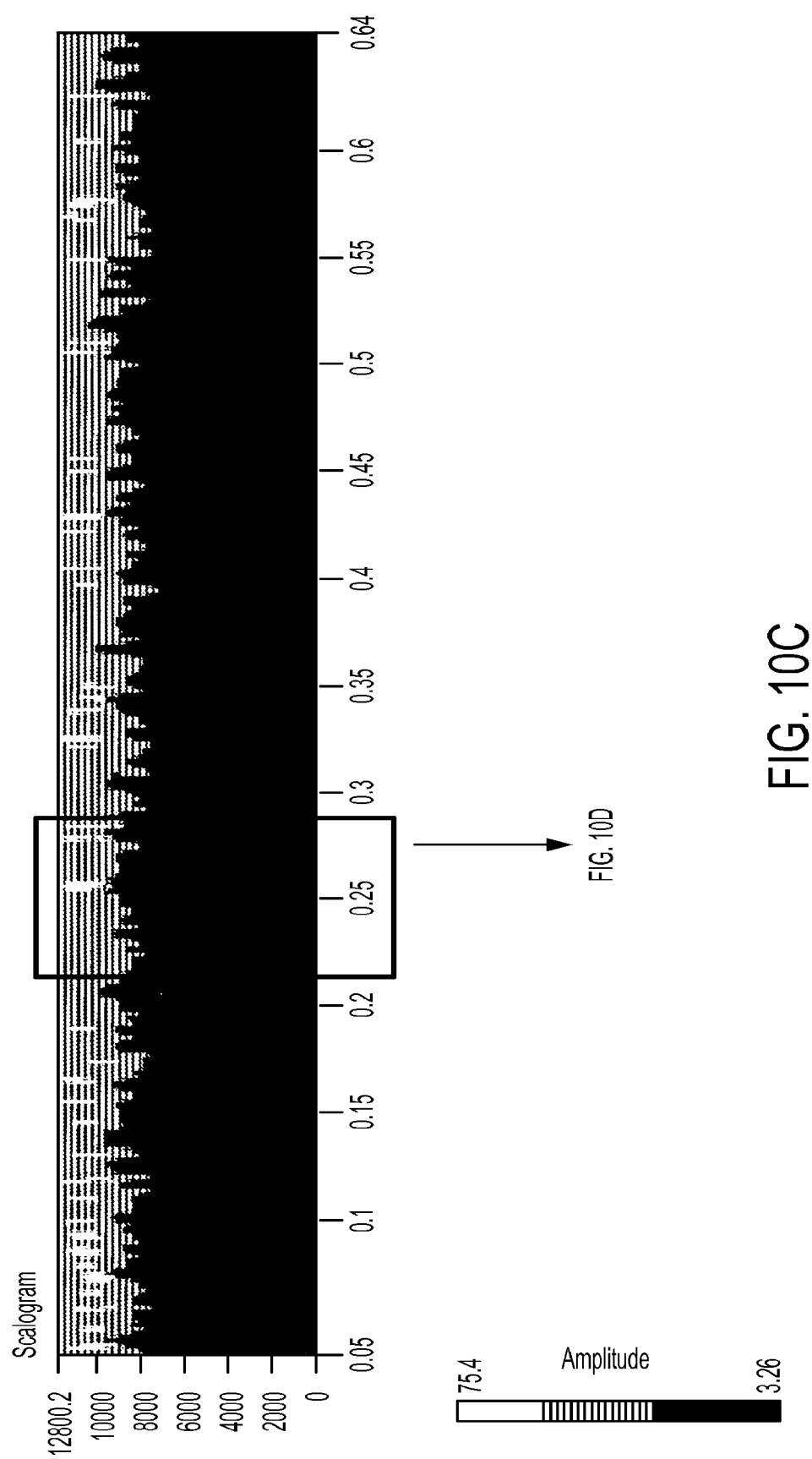
FIG. 10C is a wavelet analysis of the recorded accelerometer time waveform signal from FIG. 10A displayed as a scalogram plot.
Figure 10D:
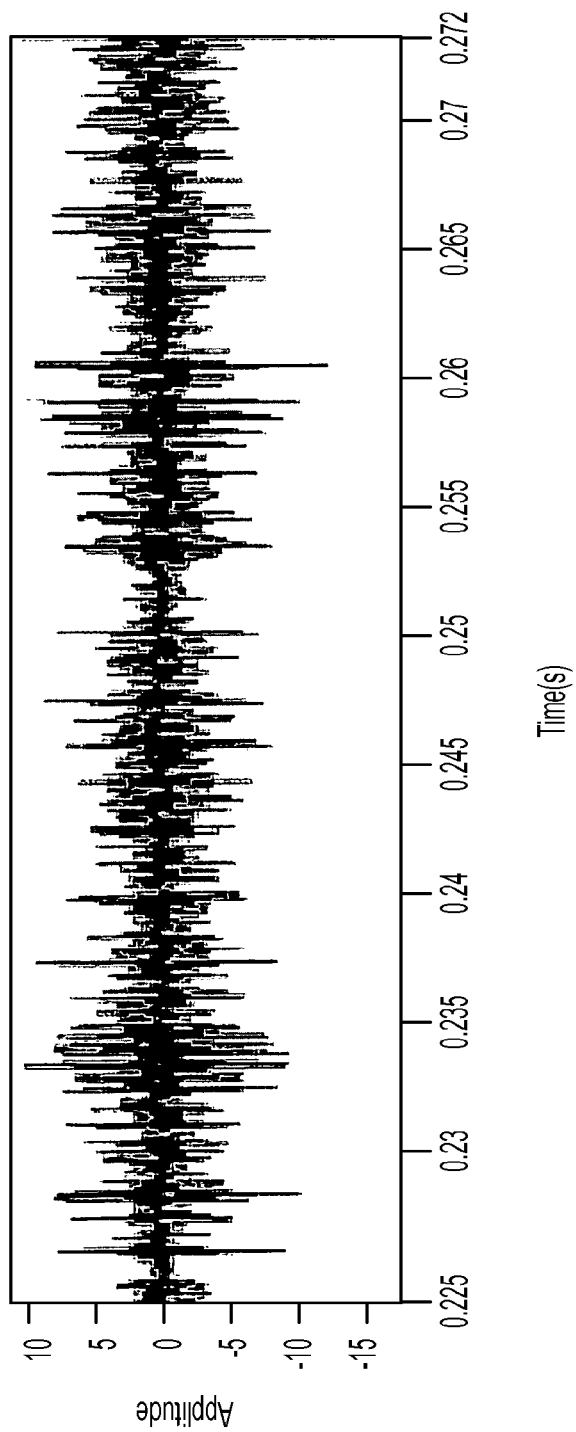
FIG. 10D is an expanded view of the waveform from FIG. 10A showing only the zone from 0.225 to 0.272 seconds.
Figure 10E:
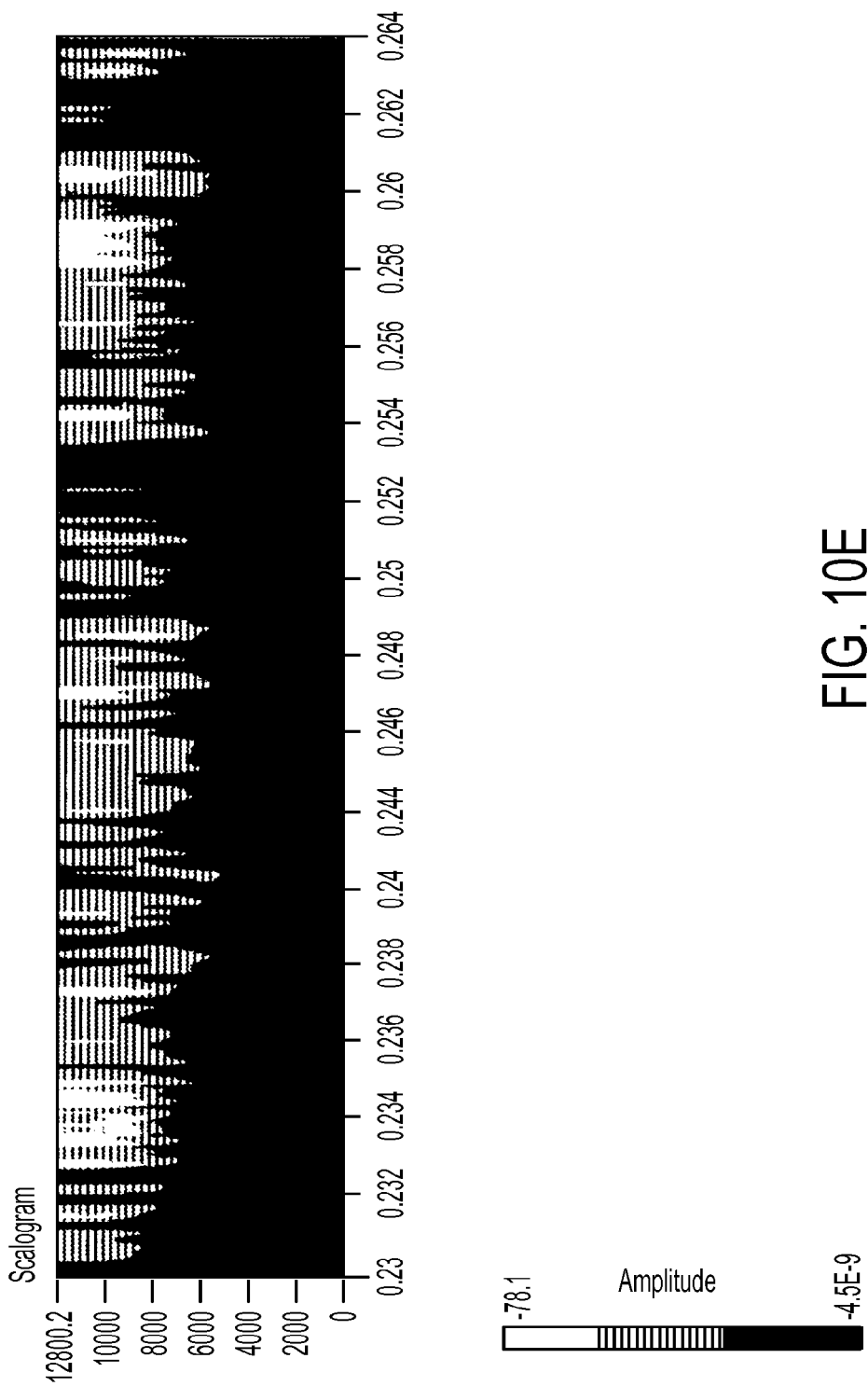
FIG. 10E is an expanded view of the scalogram plot in FIG. 10C showing only the zone from 0.23 to 0.264 seconds.

Trend data shown in FIG. 9 highlights the difference in data observed for the integrated frequency band (15-20 kHz) at conditions with and without chatter. The first section of FIG. 9 shows the integrated frequency trend when no chatter is visibly observed in the coating or dryer surface. When visible chatter did occur in the coating, a step change in the integrated frequency resulted. Monitoring different integrated frequency bands is directly applicable with the simple nσ or time integrated alarm* methods previously discussed.

In at least one embodiment of the invention, there is provided a means to monitor and alarm the early onset of chatter through wavelet analysis of the time waveform. For synchronous data collection, the time waveform represents the vibration signal measured for one complete rotation of the Yankee dryer. Taking the continuous wavelet transformation (CWT) of the time waveform sensor data parses out the vibration intensity and frequency information as a function of time. By knowing the Yankee dryer speed and diameter, a transformation from the time to the MD spatial domain is made. The MD vibration frequency and intensity is useful for tracking specific spatial zones to determine the onset of potential chatter. For example, the MD can be divided into n number of zones to trend an averaged or cumulative vibration frequency, band, or local RMS value. Alarming using either the simple nσ or time integrated approach can then be used to alert operators of potential problems. In particular, the wavelet technique will provide an early alarming condition for cases when chatter is initially developed locally before the formation of a chatter band around the dryer circumference.

An example of using the wavelet analysis on the time waveform vibration sensor to data is shown in FIG. 10. The plot labeled FIG. 10A represents the raw sensor data or waveform collected from a sensor mounted on the doctor back as shown in FIG. 1. The data was collected over 0.64 seconds representing one cylinder revolution. Spectral features and intensity from the FFT analysis (plot labeled FIG. 10B) is the integrated result over 0.64 seconds, so the strong frequency bands observed near 7800 and 11800 Hz represents the accumulated effect. Identifying unique spectral features from the FFT is useful in data interpretation, but lacks temporal information. Wavelet analysis of the waveform addresses this issue by extracting vibration frequency and intensity information at different times. By applying wavelet analysis to the waveform, a scalogram plot is constructed (labeled FIG. 10C) to display the square magnitude of the complex wavelet coefficients from the CWT to display frequency and intensity as a function of time. Expanded views of the waveform (labeled FIG. 10D) and scalogram (labeled FIG. 10E) illustrate clearly the correlation between the waveform features and spatial vibration frequencies. For example, in the zone between 0.234 and 0.236 seconds an intense band of vibration frequencies >10 kHz is observed. This frequency band shows up sporadically throughout the scalogram, but at this particular time (location), the intensity is maximum indicating localized intense high frequency vibration.

Figure 11:
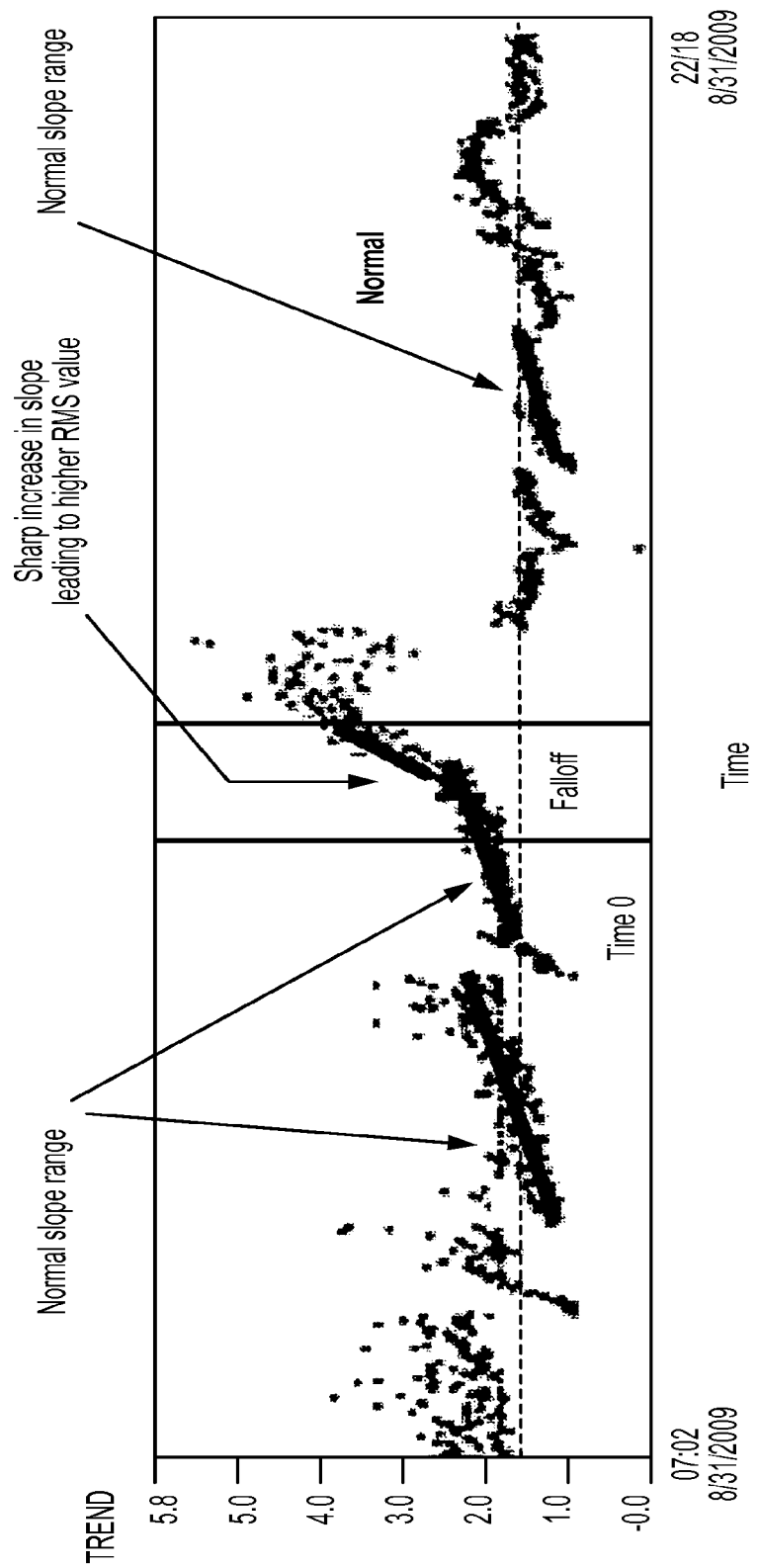
FIG. 11 is a graph of slope analysis of RMS trend data.

In at least one embodiment of the invention, there is a means to monitor the onset of early chatter detection by slope analysis of the vibration frequency band or RMS trend. A characteristic feature for trend plots of RMS or selected vibration frequency bands is the effect of the creping doctor blade age. A newly installed blade causes an initial decrease in the RMS trend. As the blade ages and wears the trend signal will increase over time. Tracking the characteristic features of the trend such as the slope and marginal slope (2.sup.nd derivative) are indicators of the process state used in assessing whether a potential chatter condition is approaching. FIG. 11 shows variations in the RMS trend slope that occurs under "normal" conditions between doctor blade changes. Cases where the RMS increases to higher level than the normal running baseline is often preceded by a sharp increase in the slope. Tracking the slope then provides a means of predicting whether the RMS value is moving toward a higher trajectory.

In at least one embodiment of the invention, the method comprises a simple alerting method based on the time integrated alarm* value that could be color coded or audible. Color coded alarming utilizes a set of colors to indicate the current alarming state, e.g., green for normal operation, yellow for an approaching chatter condition, and red for the presence of a potential critical chatter condition. In this case, the time integrated chatter condition accounts for both low and high RMS values above the alarm level at long and short time durations respectively.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments described herein and incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method of detecting and addressing chatter from a doctor blade, the method comprising:
receiving vibration data from one or more sensors associated with the doctor blade over time during a creping process, a cleaning process, or a cut-off operation in a papermaking process, wherein the vibration data comprises a series of side-to-side variation measurements over time for the doctor blade during the papermaking process;
analyzing a signal based on the received vibration data;
comparing the signal to an alarm limit;
if the signal is above the alarm limit, determining a degree to which the signal is above the alarm limit;
determining a duration of time the signal remains above the alarm limit; and
if the degree to which the signal is above the alarm limit and the duration of time the signal remains above the alarm limit satisfy predetermined conditions:
determining that excessive doctor blade chatter has occurred or is likely to occur; and
performing one or more corrective actions associated with the papermaking process in response to the determining that excessive doctor blade chatter has occurred or is likely to occur,
wherein performing the one or more corrective actions comprises one or more from the group consisting of: changing a sheet moisture level, changing a coating chemistry, changing a machine speed, changing a sheet basis weight, changing a furnish composition, changing a doctor blade stick out, changing a doctor blade loading pressure, changing a dryer temperature, replacing a worn out felt, loading a cleaning blade, and eliminating external source vibrations.

2. The method of claim 1, wherein the signal comprises a raw vibration data from at least one of the one or more vibration sensors.

3. The method of claim 1, wherein the received vibration data associated with the doctor blade over time comprises a vibration data time waveform, and wherein the method further comprises the step of converting the vibration data time waveform into a frequency domain signal including a plurality of distinct vibration frequency bands.

4. The method of claim 3, wherein the signal comprises one of the plurality of distinct vibration frequency bands in the frequency domain signal.

5. The method of claim 4, further comprising calculating an RMS frequency signal from the plurality of distinct vibration frequency bands, and wherein the signal comprises the RMS frequency signal.

6. The method of claim 5, further comprising calculating an alarm strength value based on the RMS frequency signal.

7. The method of claim 3, further comprising:
calculating an RMS frequency signal from the plurality of distinct vibration frequency bands;
calculating an alarm strength value based on the RMS frequency signal; and
calculating an alarm accumulation value corresponding to a trend of the alarm strength value over time.

8. The method of claim 3, further comprising the step of correlating characteristics of the vibration frequency bands with one or more performance properties of the doctor blade.

9. The method of claim 8, further comprising the step of defining a baseline of vibration bands based on a correlated baseline of one or more acceptable performance properties; and wherein the alarm limit comprises one or more baseline vibration band values.

10. The method of claim 8, further comprising the step of outputting when a data point on one or more of the vibration frequency bands exceeds the alarm limit.

11. The method of claim 8, wherein at least one of the one or more performance properties is selected from the list consisting of: track bearing, balance, dryer lubricity, dust levels, moisture levels, temperature, felt age, grade, furnish composition, coating chemistry, cleaning blade status, machine speed, external source vibrations, and external pressure sources.

12. The method of claim 8, wherein at least one of the correlations is determined by comparing characteristics of the vibration bands with blade age.

13. The method of claim 12, wherein comparing characteristics of the vibration bands with blade age comprises correlating a change in a slope in a saw tooth shaped vibration band with the age of the blade.

14. A method of detecting and addressing chatter from a doctor blade, the method comprising:
receiving vibration data from one or more sensors associated with the doctor blade over time during a creping process, a cleaning process, or a cut-off operation in a papermaking process, wherein the vibration data comprises a series of side-to-side variation measurements over time for the doctor blade during the papermaking process;
collecting the vibration data into a time waveform;
converting the time waveform using a fast Fourier transform to generate a converted time waveform, the converted time waveform having a frequency spectrum which includes a plurality of distinct vibration bands;
correlating characteristics of the vibration bands with one or more performance properties of the doctor blade to produce correlated vibration bands, the one or more performance properties including at least one selected from the group consisting of: track bearing, balance, dryer lubricity, dust levels, moisture levels, temperature, felt age, grade, furnish composition, coating chemistry, cleaning blade status, machine speed, external source vibrations, and external pressure sources;
determining baseline vibration bands associated with the one or more performance properties;
outputting when a data point associated with one or more vibration bands indicates excessive doctor blade chatter has occurred or is predicted to occur based on a detected degree and duration of deviation from the baseline vibration bands satisfying predetermined conditions; and
initiating one or more corrective actions associated with the papermaking process based on the output.

15. The method of claim 14, wherein the one or more corrective actions comprises one or more from the group consisting of:
changing a sheet moisture level, changing a coating chemistry, changing a machine speed, changing a sheet basis weight, changing a furnish composition, changing a doctor blade stick out, changing a doctor blade loading pressure, changing a dryer temperature, replacing a worn out felt, loading a cleaning blade, and eliminating external source vibrations.

16. The method of claim 14, wherein the one or more corrective actions is performed without interrupting the creping process, cleaning process, or cut-off operations of the papermaking process using the doctor blade.

17. The method of claim 14, further comprising calculating an RMS frequency signal from the plurality of distinct vibration frequency bands, and wherein the outputting when the data point associated with one or more vibration bands indicates excessive doctor blade chatter has occurred or is predicted to occur comprises outputting when a detected degree and duration of deviation of the RMS frequency signal from a baseline RMS frequency signal meets a predetermined condition.

18. The method of claim 14, further comprising:
calculating an RMS frequency signal from the plurality of distinct vibration bands;
calculating an alarm strength value based on the RMS frequency signal; and
calculating an alarm accumulation value corresponding to a trend of the alarm strength value over time.

19. The method of claim 14, wherein at least one of the correlations is determined by comparing characteristics of the vibration bands with blade age.

20. The method of claim 19, wherein comparing characteristics of the vibration bands with blade age comprises correlating a change in a slope in a saw tooth shaped vibration band with the age of the same blade.

\* \* \* \* \*